United States Patent
Cummings et al.

(10) Patent No.: US 11,883,213 B2
(45) Date of Patent: Jan. 30, 2024

(54) MEDICAL DEVICE CONTAINMENT AND TRANSPORTATION SYSTEMS AND METHODS

(71) Applicant: Boston Scientific Scimed, Inc., Maple Grove, MN (US)

(72) Inventors: Nathan T. Cummings, Worcester, MA (US); Jenny Dandin, Worcester, MA (US); Michele E. Dalena, Boston, MA (US); Alyson Bolick, Boston, MA (US); Ryan LaFlamme, Ham Lake, MN (US); Joshua Talsky, Brooklyn, NY (US); Mark Collins, Cedarburg, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 205 days.

(21) Appl. No.: 16/726,588

(22) Filed: Dec. 24, 2019

(65) Prior Publication Data
US 2020/0205925 A1 Jul. 2, 2020

Related U.S. Application Data

(60) Provisional application No. 62/847,142, filed on May 13, 2019, provisional application No. 62/784,995, filed on Dec. 26, 2018.

(51) Int. Cl.
*B65D 83/10* (2006.01)
*A61B 50/30* (2016.01)
(Continued)

(52) U.S. Cl.
CPC .............. *A61B 50/30* (2016.02); *B65D 25/16* (2013.01); *B65D 51/242* (2013.01);
(Continued)

(58) Field of Classification Search
CPC . A61B 50/30; A61B 25/16; A61B 2050/0071; A61B 2050/3007; A61B 2050/3011; B65D 25/16
(Continued)

(56) References Cited

U.S. PATENT DOCUMENTS 5,531,345 A * 7/1996 Nakamura ............... H02G 3/14
220/326
5,732,821 A 3/1998 Stone et al.
(Continued)

FOREIGN PATENT DOCUMENTS

DE 202009014228 U1 3/2010
DE 202016105248 U1 12/2016
(Continued)

OTHER PUBLICATIONS

Patent Translate Powered by EPO and Google for DE102017008894A1, 11 pages.*
(Continued)

*Primary Examiner* — Luan K Bui
(74) *Attorney, Agent, or Firm* — Seager, Tufte & Wickhem, LLP

(57) ABSTRACT

A system for containing and transporting a medical device may include a container including a bottom face and surrounding side faces as a closed first end and an open second end to form an inner portion for receiving and retaining the medical device. At least a portion of one or more of the side faces may have an indentation extending along a length of the respective side face. A liner and cover may be removably enclosable about the container. The liner may be extendable over the side faces to line the inner portion of the container to an outer surface of the bottom face of the container. The cover may enclose the medical device in the container between the liner and cover. The indentation may be formed
(Continued)

into the inner portion of the container. The container may be compatibly receivable in a first transportation device in a first orientation.

14 Claims, 35 Drawing Sheets

(51) Int. Cl.
*B65D 25/16* (2006.01)
*B65D 51/24* (2006.01)
*A61B 50/00* (2016.01)

(52) U.S. Cl.
CPC ............ *A61B 2050/0071* (2016.02); *A61B 2050/3007* (2016.02); *A61B 2050/3011* (2016.02)

(58) Field of Classification Search
USPC ........ 206/363–366, 370, 438, 509, 511, 557, 206/570–572
See application file for complete search history.

(56) References Cited

U.S. PATENT DOCUMENTS

| | | | |
|---|---|---|---|
| 5,896,987 A * | 4/1999 | Bettenhausen | B65D 21/0223 206/370 |
| 6,099,812 A * | 8/2000 | Allen | A61L 2/26 206/370 |
| 6,305,567 B1 * | 10/2001 | Sulpizio | F25D 25/025 220/8 |
| 6,641,781 B2 | 11/2003 | Walta | |
| 6,749,063 B2 | 6/2004 | Parker | |
| 7,744,832 B2 | 6/2010 | Horacek et al. | |
| 8,042,688 B2 | 10/2011 | Parks et al. | |
| 8,561,820 B2 | 10/2013 | Kitt et al. | |
| 8,733,551 B2 * | 5/2014 | Parker | A61B 1/00144 206/570 |
| 8,747,739 B2 | 6/2014 | Parker et al. | |
| 8,789,695 B2 | 7/2014 | Mason | |
| 8,807,354 B2 | 8/2014 | Kitt et al. | |
| 8,939,287 B2 | 1/2015 | Markovitch | |
| 9,265,578 B2 | 2/2016 | Dacey | |
| D818,841 S | 5/2018 | Newton | |
| D819,409 S | 6/2018 | Newton | |
| 10,086,131 B2 | 10/2018 | Okihara | |
| 10,405,938 B2 | 9/2019 | Ramsey | |
| D891,777 S | 8/2020 | Newton | |
| 2004/0099666 A1 * | 5/2004 | Ordiway | B65D 41/22 220/359.1 |
| 2005/0016886 A1 * | 1/2005 | Riley | A61B 50/20 206/438 |
| 2005/0109775 A1 * | 5/2005 | Meissen | B65D 21/0212 220/23.6 |
| 2006/0191943 A1 * | 8/2006 | Dane | A61L 2/26 220/501 |
| 2006/0273084 A1 * | 12/2006 | Baker | B65D 51/00 220/23.4 |
| 2007/0215507 A1 | 9/2007 | Glenn et al. | |
| 2007/0299361 A1 | 12/2007 | Hein | |
| 2009/0183807 A1 * | 7/2009 | Sadlier | B65D 41/22 156/70 |
| 2012/0152289 A1 | 6/2012 | Smith et al. | |
| 2015/0144515 A1 | 5/2015 | Chartres et al. | |
| 2015/0257632 A1 * | 9/2015 | Ramsey | A61B 50/36 206/204 |
| 2015/0259122 A1 | 9/2015 | Parker | |
| 2016/0058518 A1 | 3/2016 | Mason | |
| 2017/0056122 A1 | 3/2017 | Ramsey | |
| 2018/0110580 A1 | 4/2018 | Hynes | |
| 2018/0134453 A1 | 5/2018 | Wassenburg | |
| 2019/0167824 A1 | 6/2019 | Rhodes et al. | |
| 2020/0205925 A1 | 7/2020 | Cummings et al. | |
| 2021/0186641 A1 | 6/2021 | Cummings et al. | |

FOREIGN PATENT DOCUMENTS

| | | |
|---|---|---|
| DE | 102017008894 A1 | 3/2018 |
| EP | 2501321 A2 | 9/2012 |
| EP | 2501321 B1 | 10/2016 |
| EP | 3288437 A1 | 3/2018 |
| GB | 2525694 A | 11/2015 |
| JP | 62-099352 | 1/1989 |
| WO | 03034936 A1 | 5/2003 |
| WO | 2015166240 A2 | 11/2015 |

OTHER PUBLICATIONS

"ETS Plus Secure Endoscope Transportation with Hygienic Focus", Olympus brochure EO428343EN (2017) 3 pages.
"Medivators™ Cleanascope™ Transport & Short Term Storage System", MEDIVATORS—A Cantel Medical Company brochure (2015) 4 pages.
"SafeCAP® Endoscope Transport and Short-Term Storage System", ClinicalChoice brochure (2019) 2 pages.
International Search Report and Written Opinion, Application No. PCT/US2019/068487, dated Apr. 22, 2020, 11 pages.

* cited by examiner

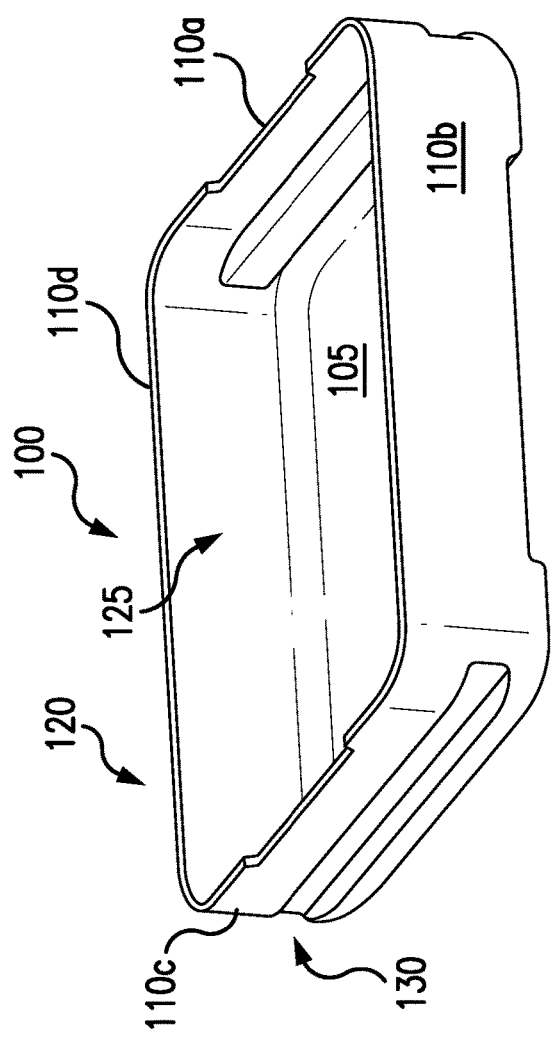
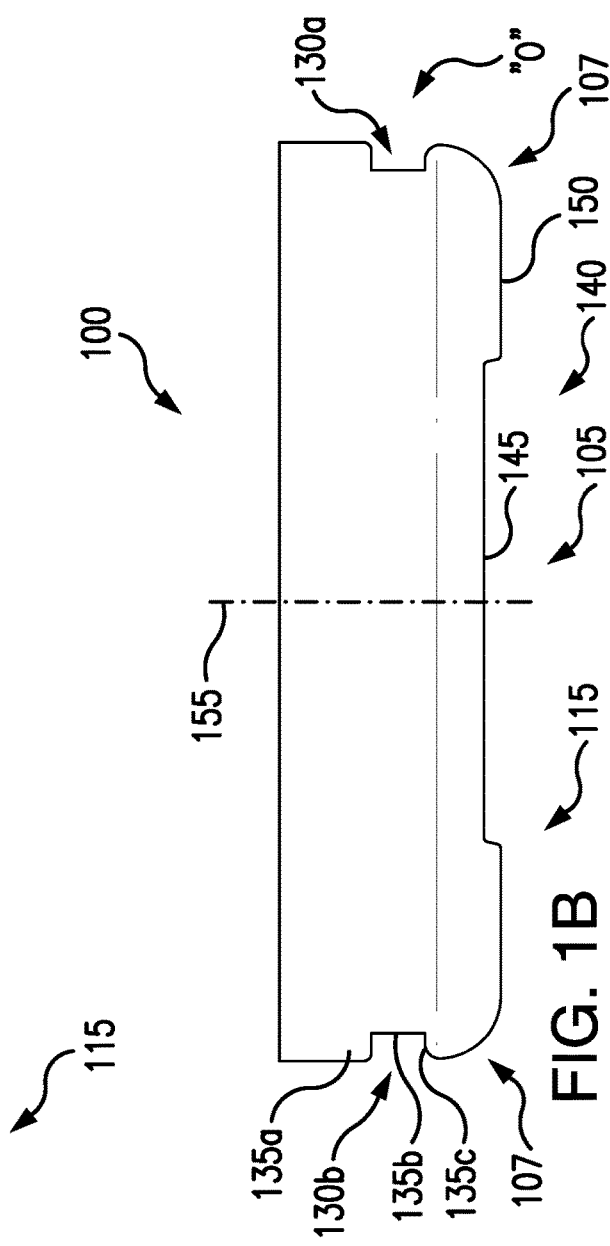
FIG. 1A
FIG. 1B

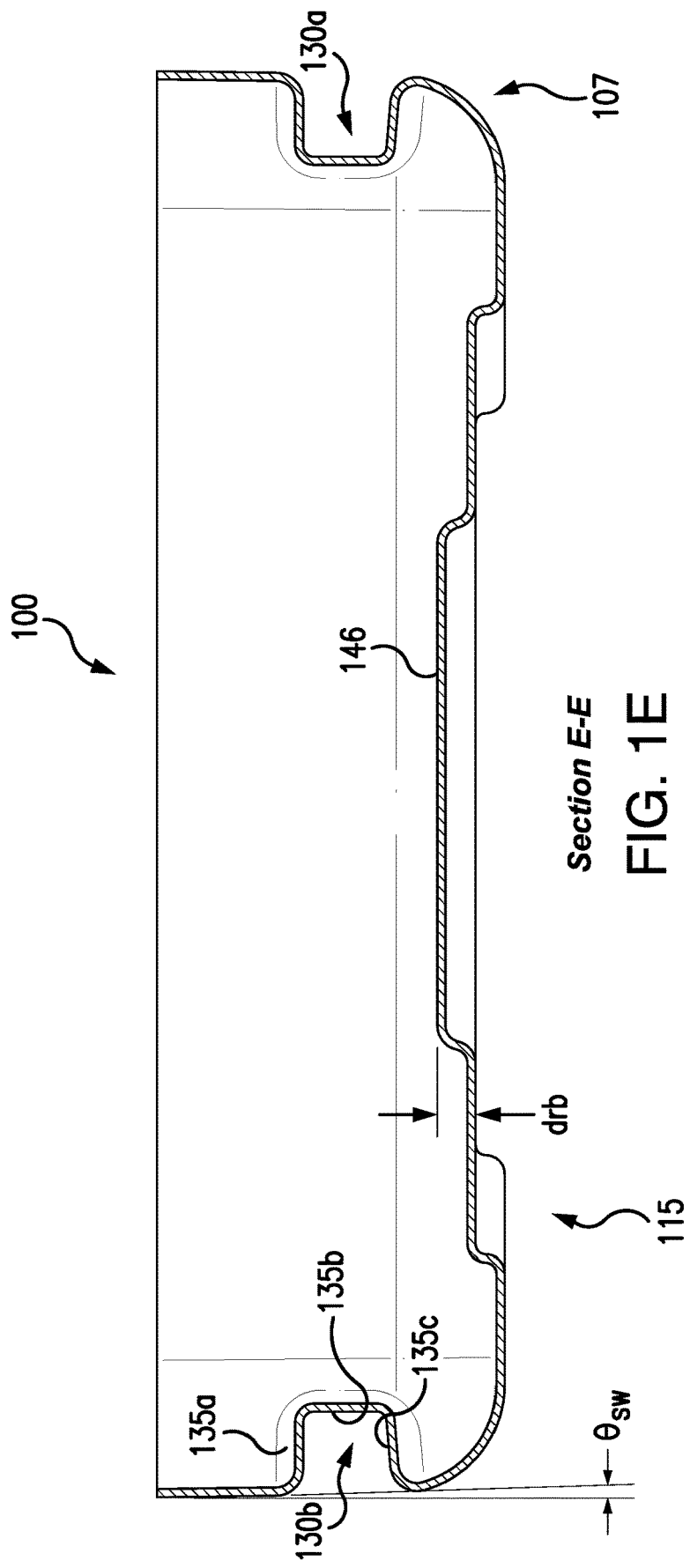

Section H-H

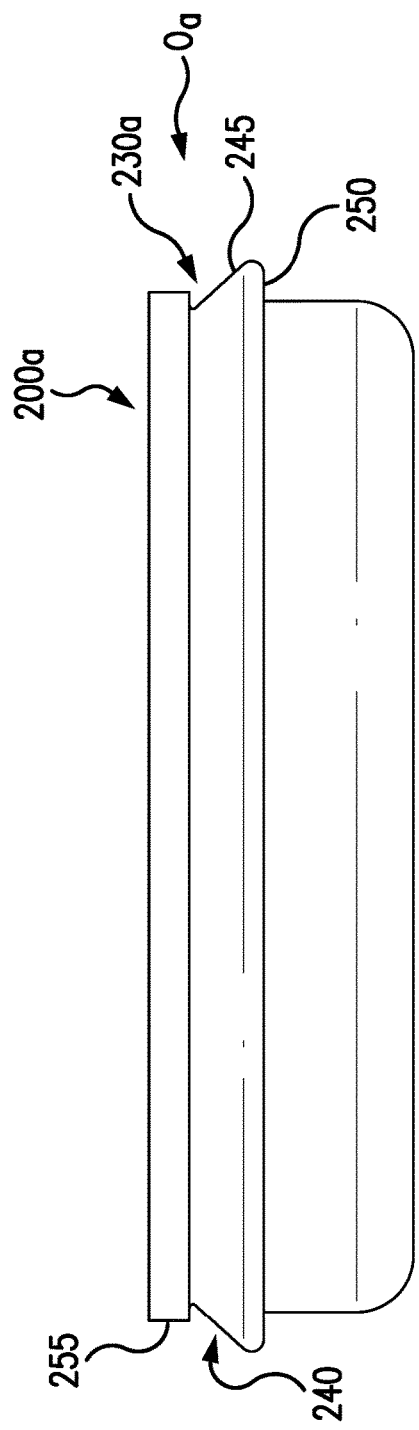
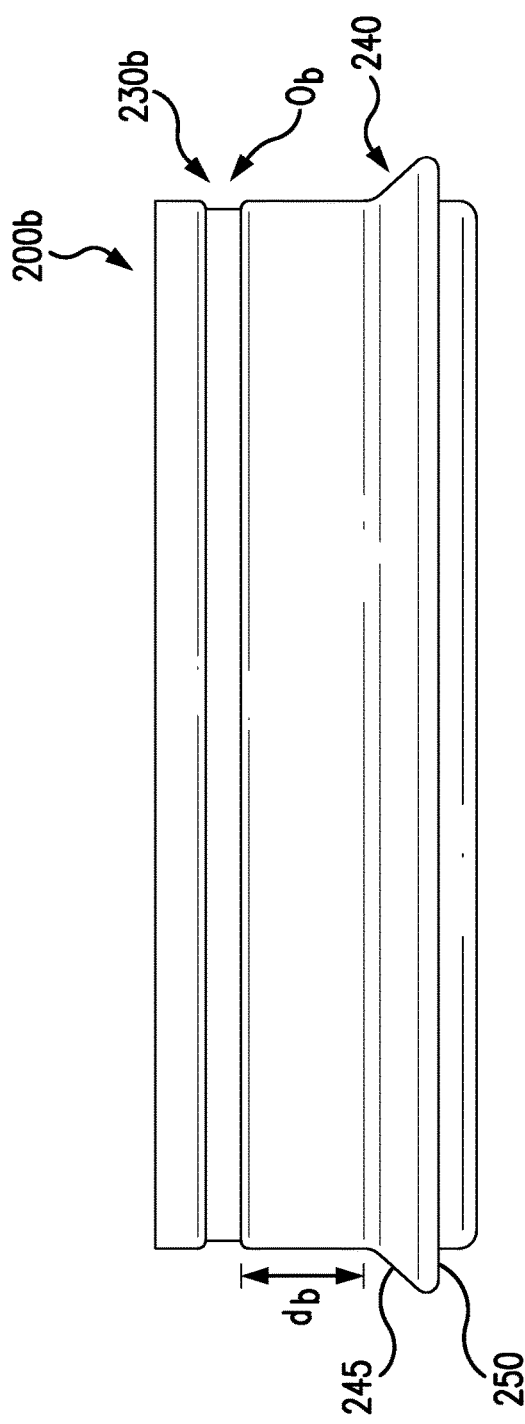
FIG. 2A
FIG. 2B

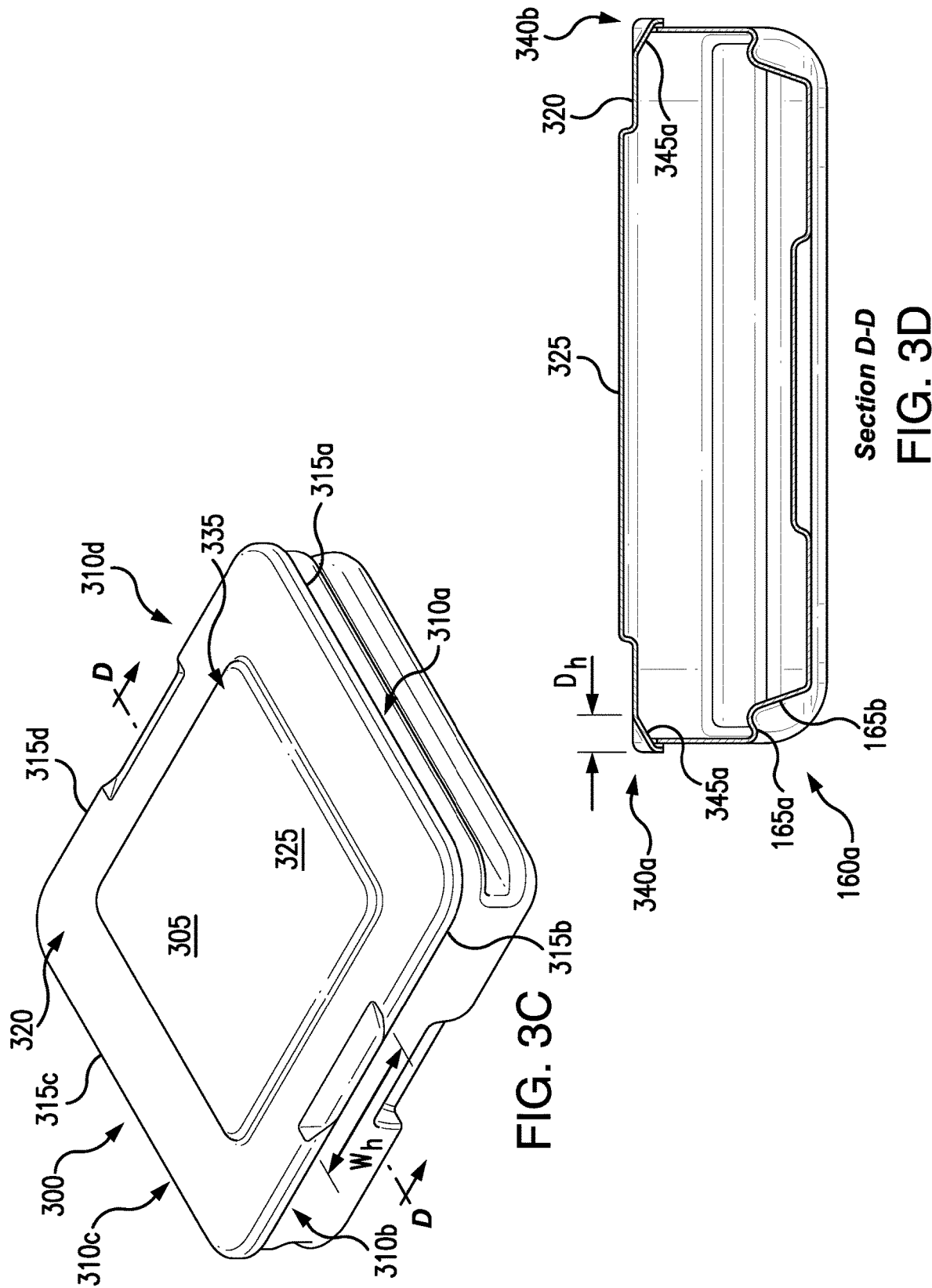

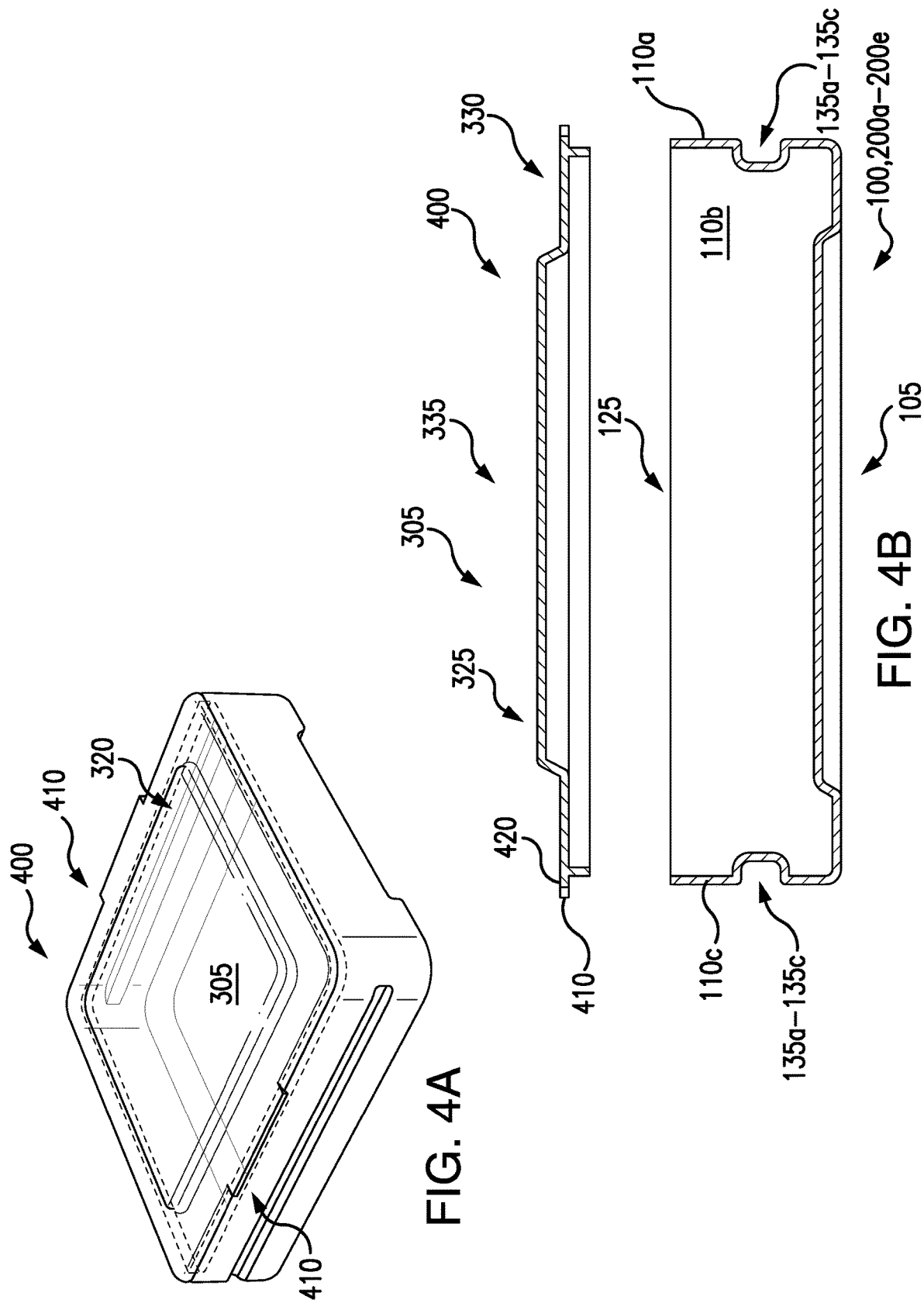

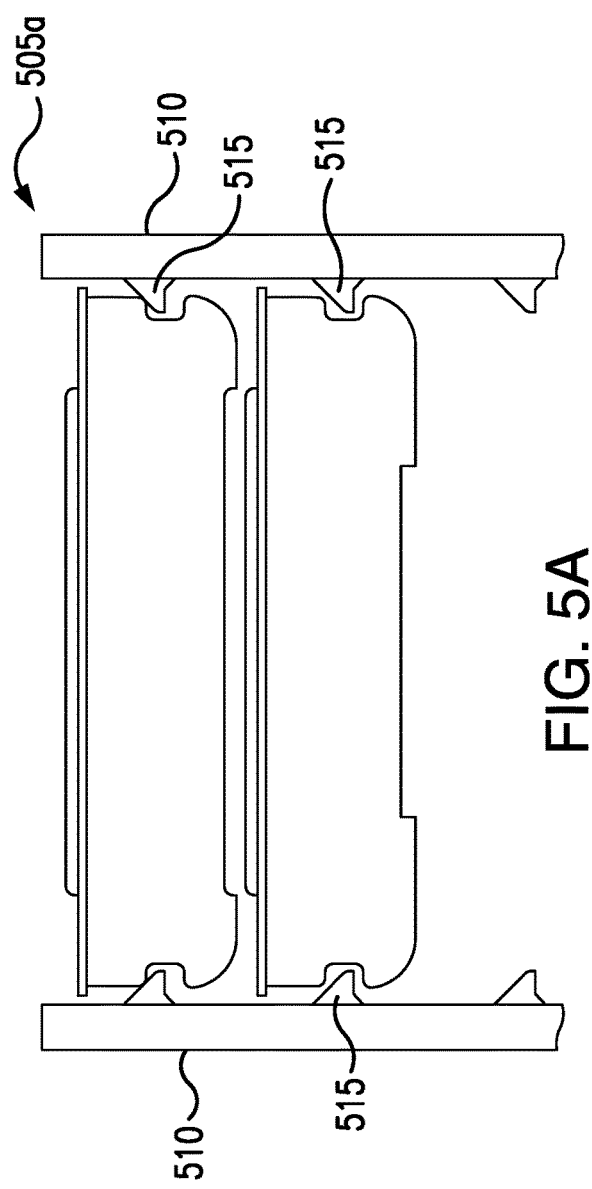
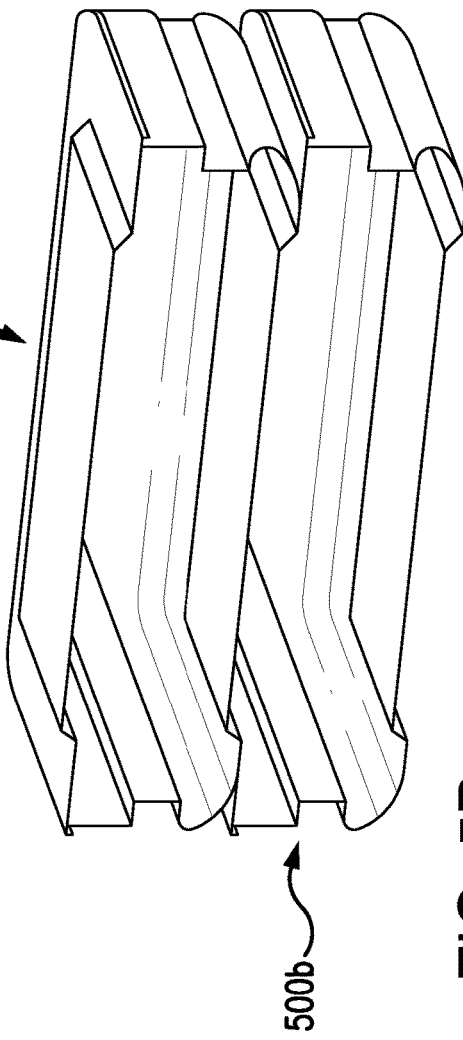
FIG. 5A
FIG. 5B

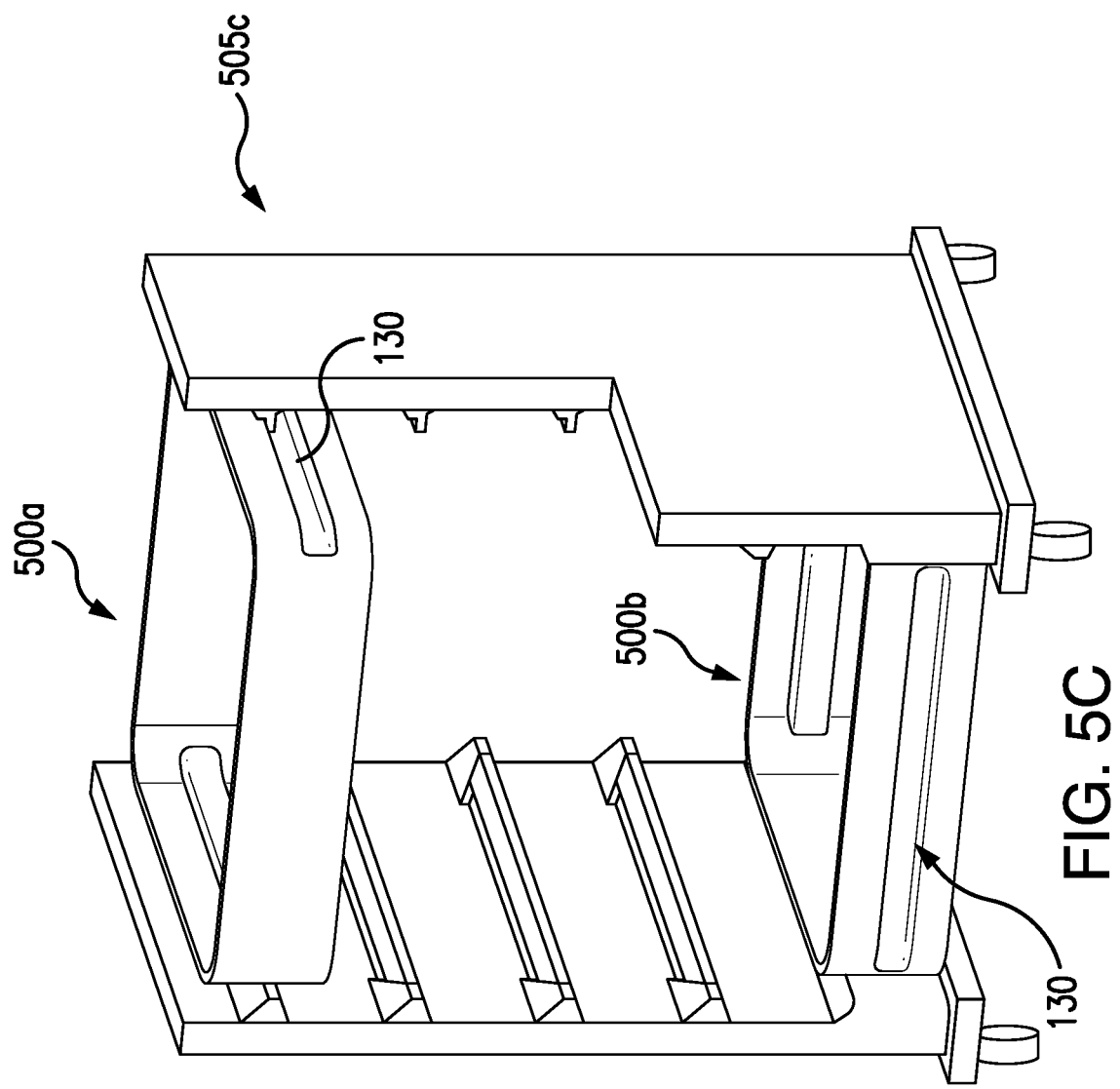

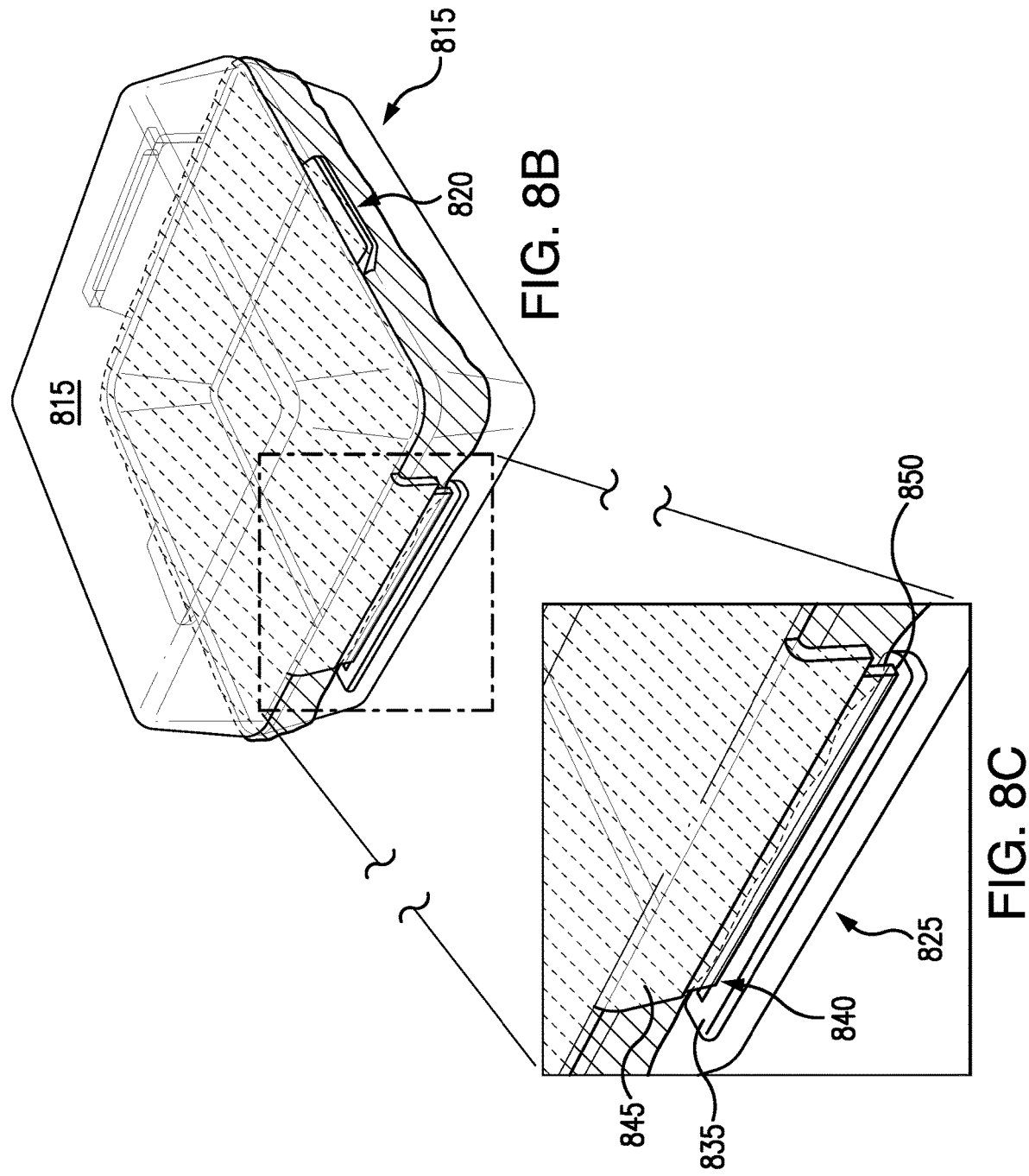

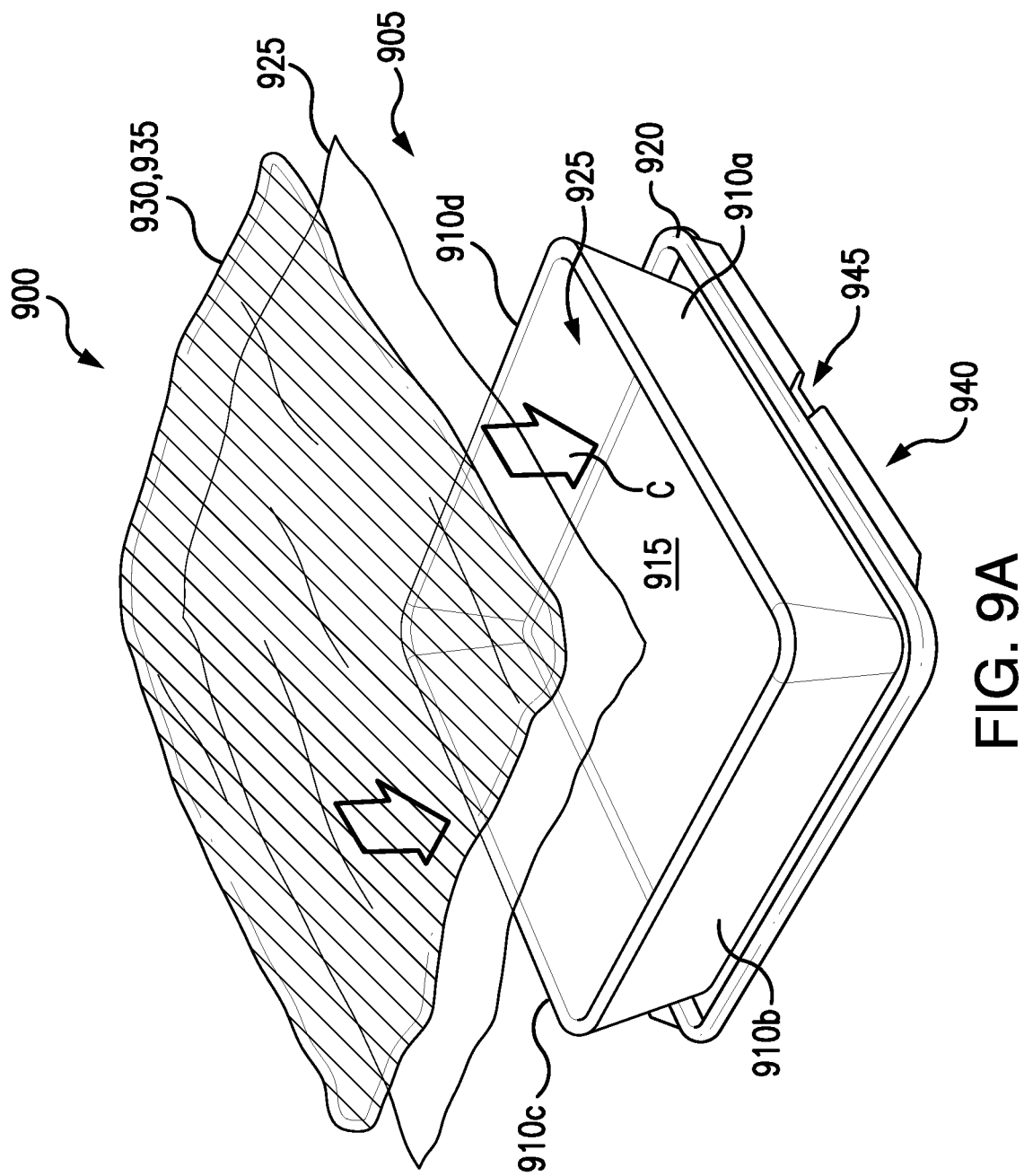

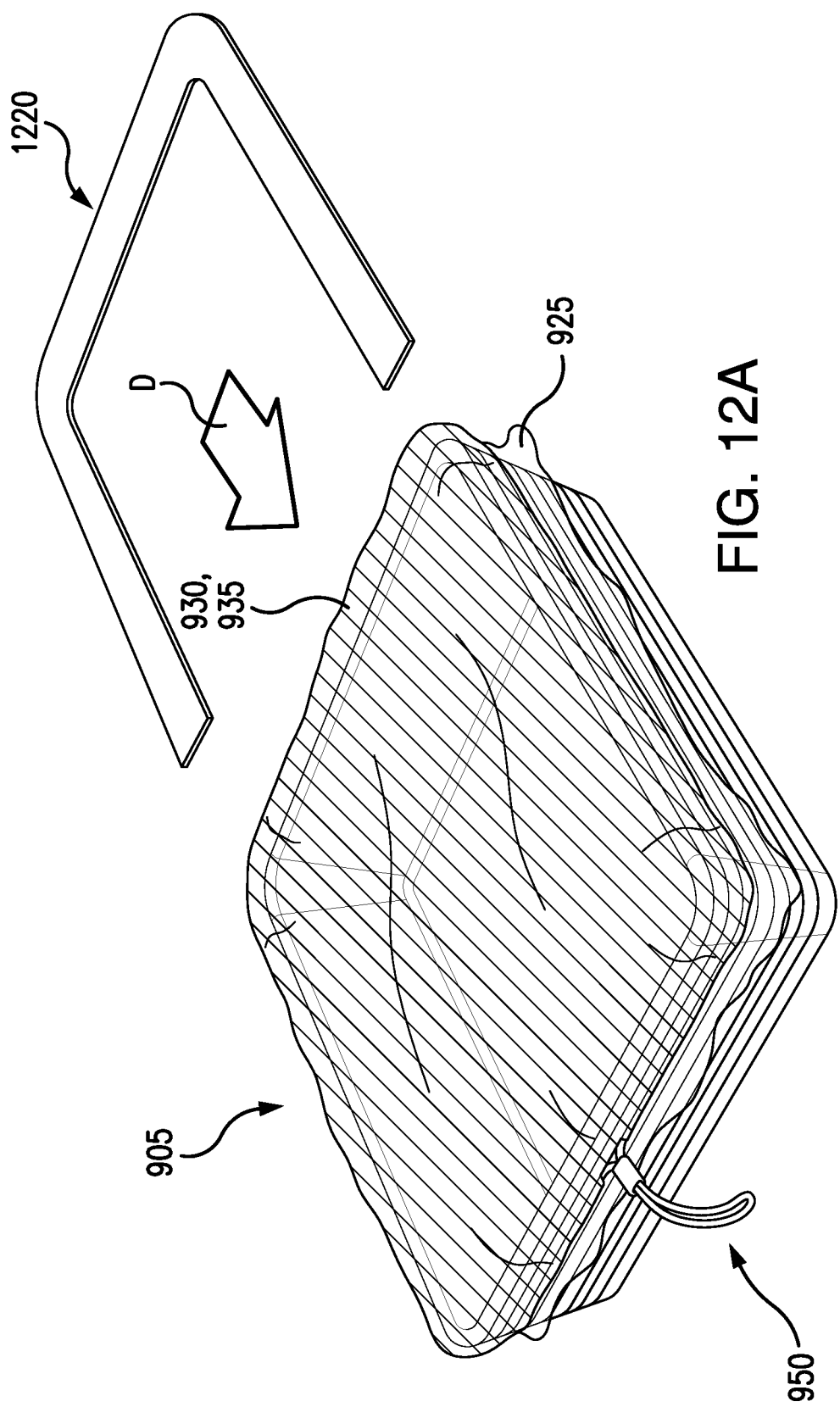

Section B-B

Section B-B

ND METHODS

CROSS-REFERENCE TO RELATED APPLICATIONS

The present disclosure claims priority to and the benefit of U.S. Provisional Patent Application Ser. No. 62/847,142, filed May 13, 2019, entitled "Medical Device Containment and Transportation Systems and Methods," and U.S. Provisional Patent Application Ser. No. 62/784,995, filed Dec. 26, 2018, entitled "Medical Device Containment and Transportation Systems and Methods," the disclosures of which are hereby incorporated by reference in their entirety.

The present disclosure is related to U.S. Provisional Patent Application 62/953,352, filed even date herewith, entitled Medical Device Transportation Systems, and U.S. Provisional Patent Application 62/953,359, filed even date herewith, entitled Medical Device Transportation Systems, the disclosures of which are hereby incorporated by reference in their entirety.

FIELD

The present disclosure relates generally to containment and transportation systems, and more particularly, containers and methods for transporting medical devices.

BACKGROUND

Some devices, including endoscopes, may be reusable for on-going patient use. Medical facilities, such as clinics or hospitals, may manually clean and high-level disinfect each device between use, and may need to transport the devices from a reprocessing or storage location to another location for use in a medical procedure. Clean medical devices may be deliverable to the medical professional for performing a medical procedure and used medical devices may be deliverable to the reprocessing or storage location.

One challenge for medical facilities is to maintain a workflow of the clean and used medical devices to minimize cross-contamination and a potential spread of infections and/or diseases. Current medical device containment and transportation systems used in medical facilities may be difficult to clean, e.g., including configurations that may allow for bacteria and other contaminants to remain on the surfaces even after disinfecting processes. Clean medical devices may be at risk of contamination in the event the containment systems are not thoroughly disinfected.

Additionally, existing containment and transportation systems may only be used exclusively together, so that medical facilities may be limited to a particular container to be used with a transportation system. Thus, medical facilities may be unable to swap out particular container configurations in different types of transportation systems as desired.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a system for containing and transporting a medical device may include a container including a bottom face and surrounding side faces as a closed first end and an open second end to form an inner portion for receiving and retaining the medical device. At least a portion of one or more of the side faces may have an indentation extending along a length of the respective side face. A liner may be removably enclosable about or attachable to the container. The liner may be extendable over the side faces to line the inner portion of the container to an outer surface of the bottom face of the container. The liner may be conformable to a profile of the container. The indentation may be formed into the inner portion of the container such that the container is compatibly receivable in a first transportation device in a first orientation.

In various of the foregoing and other embodiments of the present disclosure, the bottom face of the container may include a contour, such that the container may be compatibly receivable in the first transportation device in a second orientation different from the first orientation. A lid may be removably attachable to the open second end of the container, and the lid may be extendable over the side faces to enclose the inner portion of the container. A lid may be removably attachable to the open second end of the container. The lid may be at least partially insertable in the inner portion of the container, such that an overhang of the lid may contact an upper edge of the side faces of the container. A contour of the lid may be formed to mate with the bottom face contour of the container, such that a plurality of containers and lids may be stackable in alignment with each other. The lid may include one or more handles. A first cover may be removably enclosable about or attachable to the container and extendable over at least a portion of the side faces and across the open second end of the container to enclose the inner portion. A second cover may be removably enclosable about or attachable to the container and extendable over at least a portion of the side faces and across the open second end of the container to enclose the inner portion. The first cover may be exchangeable with the second cover for visual verification of a condition of the medical device. The first cover may be reversible, as opposed to a second cover, with each side of the reversible cover for visual verification of a different condition of the medical device. The container may be compatibly receivable in a second transportation device. The second transportation device may be different from the first transportation device, such that the container may be exchangeable between the first transportation device and the second transportation device. The liner may be removably enclosable about or attachable to the container by an elastic opening, drawstring, or a securement, or combinations thereof. One or more handles may be formed in a container as indentations in the side face, bottom face, or the corner between a side face and the bottom face, or some combination thereof. The handles may be formed with a width, depth and height sized to accommodate a user's fingers when grasping the container. Handles on the lid may be formed to complement handles on the container, so that one may grasp a container handle and lid handle together with the fingers and thumb of one hand. The side faces of a container may extend along a straight line from the open second end to the closed first end vertical to the bottom face, or the side faces may extend along a straight line that tapers inward from vertical from the open second end to the closed first end, or some side faces may be vertical while others may be tapered inward. The indentations formed into the inner portion of a container may have a uniform height of opening along the length of the indentation, or the opening may increase in height toward one or both ends of the indentation, such that the container may be further compatibly receivable in a transportation device. The contour of the bottom face of the container may include an indentation that may extend from the bottom face into the inner portion of the container in order to form a space along the bottom face that may accommodate gathered edges of a liner extendable over the side faces and an outer surface of the bottom face of the container.

According to an exemplary embodiment of the present disclosure, a container for containing and transporting a medical device may include a bottom face and surrounding side faces as a closed first end and an open second end to form an inner portion for receiving and retaining the medical device. At least a portion of one or more of the side faces may have a first indentation extending along a length of the respective side face. The first indentation on the at least a portion of the one or more side faces may be formed into the inner portion of the container. The container may be compatible to be receivable in a first transportation device.

In various of the foregoing and other embodiments of the present disclosure, a protrusion may extend from at least a portion of one or more of the side faces and may be positionable relative to the first indentation on at least the portion of the one or more side faces of the container. The portion of one or more of the side faces of the container may include a second indentation. A liner may be removably enclosable about or attachable to the container. The liner may be extendable over the side faces and engageable with the first or second indentation to line the inner portion of the container, such that the liner may be conformable to a profile of the container. The container may be compatibly receivable in a second transportation device. The second transportation device may be different from the first transportation device, such that the container may be exchangeable between the first transportation device and the second transportation device. A lid may be removably attachable to the open second end of the container to enclose the inner portion of the container.

According to an exemplary embodiment of the present disclosure, a method for containing and transporting a medical device may include attaching a liner to a container. The container may include a bottom face and surrounding side faces as a closed first end and an open second end to form an inner portion. At least a portion of one or more of the side faces may have an indentation extending along a length of the respective side face. The liner may be extendable over the side faces and the inner portion of the container to an outer surface of the bottom face of the container, such that the liner may be conformable to a profile of the container. A medical device may be received in the inner portion of the container. A first cover may be enclosed about or attachable to the container. The first cover may extend over at least a portion of the side faces and across the open second end of the container to enclose the inner portion. The first cover may be exchangeable with a second cover for visual verification of a condition of the medical device. The first cover may be reversible, as opposed to a second cover, with each side of the reversible cover for visual verification of a different condition of the medical device. The indentation may be formed into the inner portion of the container such that the container may be compatibly receivable in a first transportation device in a first orientation. The bottom face of the container may include a contour, such that the container may be compatibly receivable in the first transportation device in a second orientation different from the first orientation. A lid may be attached to the open second end of the container to enclose the inner portion of the container. The container may be compatibly receivable in a second transportation device. The second transportation device may be different from the first transportation device, such that the container may be exchangeable between the first transportation device and the second transportation device. The first cover may be exchanged with the second cover in response to a change in the condition of the medical device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A-1C illustrate an exemplary embodiment of a container in accordance with the present disclosure;

FIGS. 1D-1G illustrate an exemplary embodiment of a container in accordance with the present disclosure;

FIGS. 2A-2E illustrate exemplary embodiments of a container in accordance with the present disclosure;

FIGS. 3C-3D illustrate an exemplary embodiment of a lid with a handle feature for a container in accordance with the present disclosure;

FIGS. 4A-4B illustrate an exemplary embodiment of a lid for a container in accordance with the present disclosure;

FIG. 5A illustrates partial view of an exemplary embodiment of a containment and transportation system in accordance with the present disclosure;

FIG. 5B illustrates a cross-sectional view of an exemplary embodiment of a plurality of containers in a stacked configuration in accordance with the present disclosure;

FIGS. 5C-5D illustrate exemplary embodiments of a containment system in accordance with the present disclosure;

FIGS. 8A-8C illustrate an exemplary embodiment of a containment system in accordance with the present disclosure;

FIGS. 9A-9B illustrate an exemplary embodiment of a containment system in accordance with the present disclosure;

FIGS. 12A-12B illustrate an exemplary embodiment of a containment system in accordance with the present disclosure;

DETAILED DESCRIPTION

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Exemplary embodiments of containment and transportation systems and methods according to the present disclosure may be configured for improved cleanability or disinfection, to reduce a risk of contamination of medical devices. Exemplary embodiments may also be configured to minimize or prevent inadvertent re-use of a device that has not been reprocessed, and/or inadvertently reprocessing an already reprocessed device that is thought to have been used. As described above, existing systems may be configured with features such as undercuts, lips, notches, or the like, that may trap contaminants. During handling, a medical professional may contact the contaminated undercut or lip, potentially transferring contaminants to a clean medical device and thereby increasing a risk of spreading diseases to a patient.

Figure 1C:
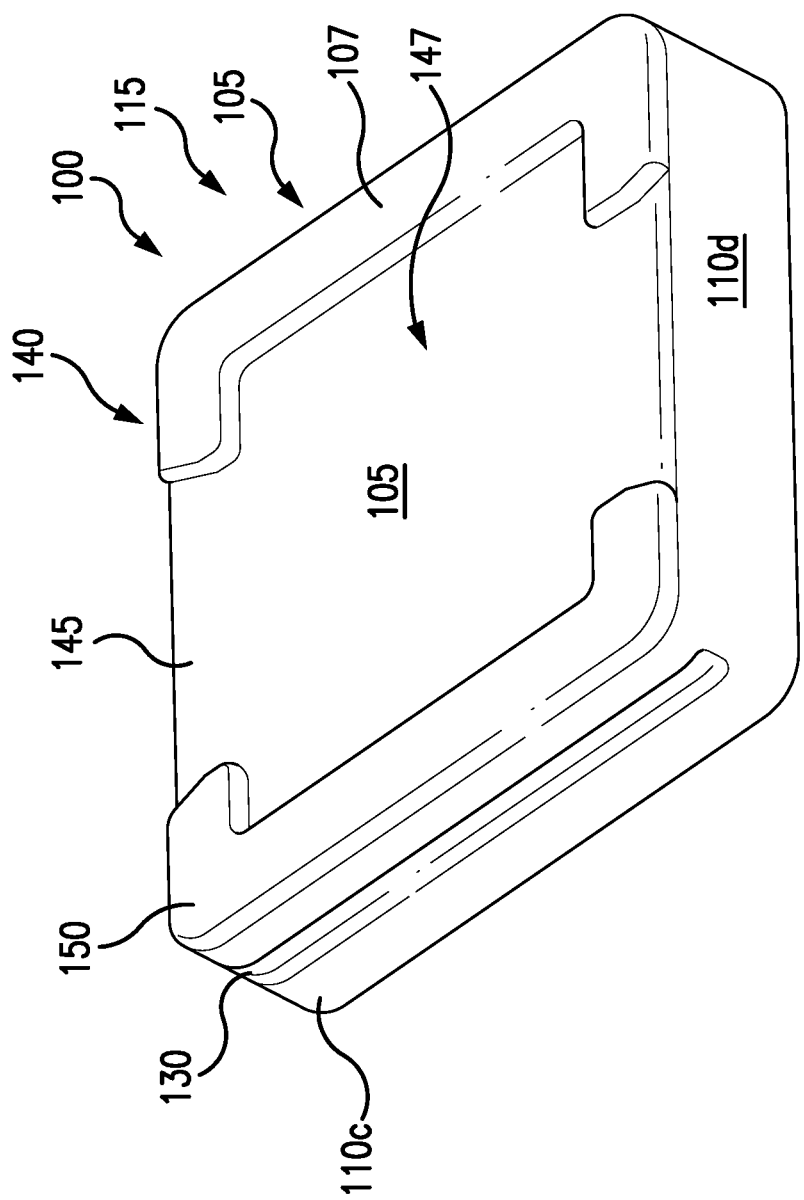

A containment system in accordance with the present disclosure may include a container having an improved design to minimize contamination for receiving, handling and retaining a medical device, which may be transported throughout a medical facility for reprocessing and patient use. Referring now to FIGS. 1A-1G, an exemplary embodiment of a container 100 is depicted. The container 100 may be formed as a tray, or basket, or a shallower-type of receptacle, for receiving and retaining a medical device. The container 100 may have a bottom face 105, and surrounding side faces 110a-110d, to form the container having a closed first end 115 and an open second end 120. The open-ended container 100 may have an inner portion 125 formed by the bottom face 105 and surrounding side faces 110a-110d, e.g., such that a medical device is receivable by placement on the bottom face 105 and retainable inside the container by the surrounding side faces 110a-110d. In some embodiments, the side faces 110a-110d may extend along a straight line that is vertical to the bottom face 105 (e.g., FIGS. 1A-1C), and in other embodiments one or more of side faces 110a-110d may extend along a straight line that tapers inward from the open second end 120 to the closed first end 115. For example, referring to FIGS. 1D-1L, the container 100 may include vertical sides faces 110b, 110d along the front and back of the container, while side faces 110a, 110c along the sides of the container including indentations 130 may taper slightly inward from vertical extending from the open second end 120 to the closed first end 115. FIG. 1E depicts a taper of $\theta_{sw}$ degrees from vertical that may be a range of 0 degrees to about five degrees. The taper may help to provide clearance between side surfaces 110a, 110c of the container and the sides of a transportation device when the container is loaded in the device. Alternatively, or additionally, the taper may help in the manufacturing process for the container, e.g., to aid in releasing the container from an injection mold if that forming technique is used.

In some embodiments, the container 100 may be formed as a rectangle, or square, e.g., having four side faces 110a-110d, although it is envisioned that the container may be formed with any number "n" of side faces. Additionally, the container 100 may have rounded edges 107 connecting the bottom face and surrounding side faces, which may be advantageous for a more thorough disinfection as well as handling. In embodiments with a tapered side face, the side face may be made to follow a straight line from the open second end to the closed first end and tangential to the apex of the rounded edge 107 (see FIG. 1E). The container may be formed of a substantially rigid material, such as a plastic or composite, and may be thermoformed or molded as a single piece to its configuration.

The container 100 may have one or more indentations 130. In embodiments, a first indentation 130a may extend along at least a portion of a first side face 110a, e.g., substantially parallel to the bottom face 105. Similarly, a second indentation 130a may extend along at least a portion of a third side face 110c, e.g., substantially parallel to the bottom face 105 and in alignment with the first indentation 130a. The indentations may extend along the full length of the respective face, although in some embodiments the indentations may extend along a portion of the side face. In some embodiments, the container 100 may have two indentations 130a, 130b, along opposing side faces, to be received by a transportation device. Indentations may also be included in at least a portion of the other side faces 110b, 110d, etc. The indentations 130 may be substantially symmetrical to each other, e.g., so that the container 100 may be receivable into a transportation device in an upright position. In embodiments, the container may be receivable into a cart, for transport in a medical facility.

The indentations 130 may be formed to extend inward into the inner portion 125. In some embodiments, the indentations 130 may be formed as rails, e.g., having a rectangular cross-section. The indentations may be formed inward so that a user, e.g., a medical professional, may grip the container 100 by the indentations 130 (e.g., surfaces 135a). The medical professional may alternatively and/or additionally handle the container 100 via the bottom face 105 and/or side faces 110a-110d (e.g., rounded edges 107). In embodiments, the medical professional may slide a container 100 in and out of a transportation device, such as a cart, and may carry the container 100 to a reprocessing location and/or a patient procedure location. The indentations 130 may have surfaces 135a-135c formed substantially perpendicular to each other (90 degrees±10 degrees), although in some embodiments one or more of the surfaces may form an obtuse angle (≥90 degrees). For example, surface 135a may slope down slightly as it approaches surface 135b, so as to form an angle of approximately 90.5 degrees to vertical surface 135b. As a further example, surface 135c may be at an angle Ω of approximately 104 degrees to surface 135b, such that surface 135c slopes downward toward the bottom surface 105 as the surface 135c extends to the side surface of the container 100 (see, e.g., FIG. 1L). The surfaces 135a-135c of the indentations 130 may be cleanable, e.g., contaminants may not be trapped in the indentations, so that when the medical professional grips and carries the container 100 as needed, cross-contamination may be minimized. In embodiments, corners of the surfaces 135a-135c may have radii to enhance cleanability of the container 100, which may be dimensioned between approximately 0.100 to 0.180 inches for cleaning (see e.g., FIG. 4B). The surfaces 135a-135c may be a "C" or "U" shape, to create an opening "o". As described below, the opening "o" may be sized as desired, e.g., to allow for handling by a medical professional and/or for receiving a cover, a liner, or both, e.g., based on the surface 135b formed substantially perpendicular relative to the bottom face 105.

In some embodiments, the indentations 130 may have a uniform height of opening along the side face (e.g., FIG. 1C), and in other embodiments the indentions may have a height of opening that increases at one or both ends of the indentation. Referring to FIG. 1F, container 100 includes indentations 130 extending along the side faces 110a, 110c, with flared end openings 132. The height of the middle length of indentation 130 is represented as $d_{CI}$ and the height of the flared end openings 132 is represented as $d_{TT}$. Height $d_{TT}$ may gradually decease to height $d_{CI}$ through the length of the flare end openings 132. For example, at a maximum height, flared end openings 132 may be approximately 30%-50% greater than the height of the middle length of indentations 130. Flare end openings may assist with aligning the opening of indentation 130 with the rails 515 of a transportation device 505a, 505c, as the container is loaded into the device. Flare end openings 132 may also provide some gap clearance between the edges of the opening of indentation 130 and the edges of rails 515 to facilitate sliding the container into a transportation device along the rails. In some embodiments, one or both ends of indentations 130, whether flared or not, may include a portion 135d that wraps around from the side face with the indentation to the adjacent side face (see, e.g., FIG. 1D). This may assist with alignment and starting the indentation along the rails of a transportation device once aligned.

In embodiments, the indentations 130 may be formed to allow for the container 100 to be compatibly receivable into a plurality of transportation devices. For example, the container 100 may be receivable in a first transportation device, and a second transportation device, where the first and second transportation devices have differing configurations. It is understood that the container may be compatibly receivable in any number "n" of transportation devices of differing configurations. The indentations may extend inwardly into the inner portion 125 a depth such that the container is adaptably receivable into carts having different configurations. In some embodiments, the container 100 and the indentations 130 may be dimensioned to be receivable in the transportation devices. In this matter, the container 100 may be compatible with a variety of transportation systems (see FIGS. 5A, 5C, 5D, 5E).

The bottom face 105 of the container 100 may include a contour 140. The contour 140 may include recessed portions 145, e.g., an outer surface 148 of the bottom face 105 may be disposed inward from portions 150 of the bottom face 105. The recessed portions 145 may be positioned substantially along the side faces 110b, 110d opposite of side faces having the indentations 130a, 130b, and/or along a central portion 147 of the bottom face 105. In some embodiments, side faces 110a, 110c may have at least the portions 150.

Figure 1D:
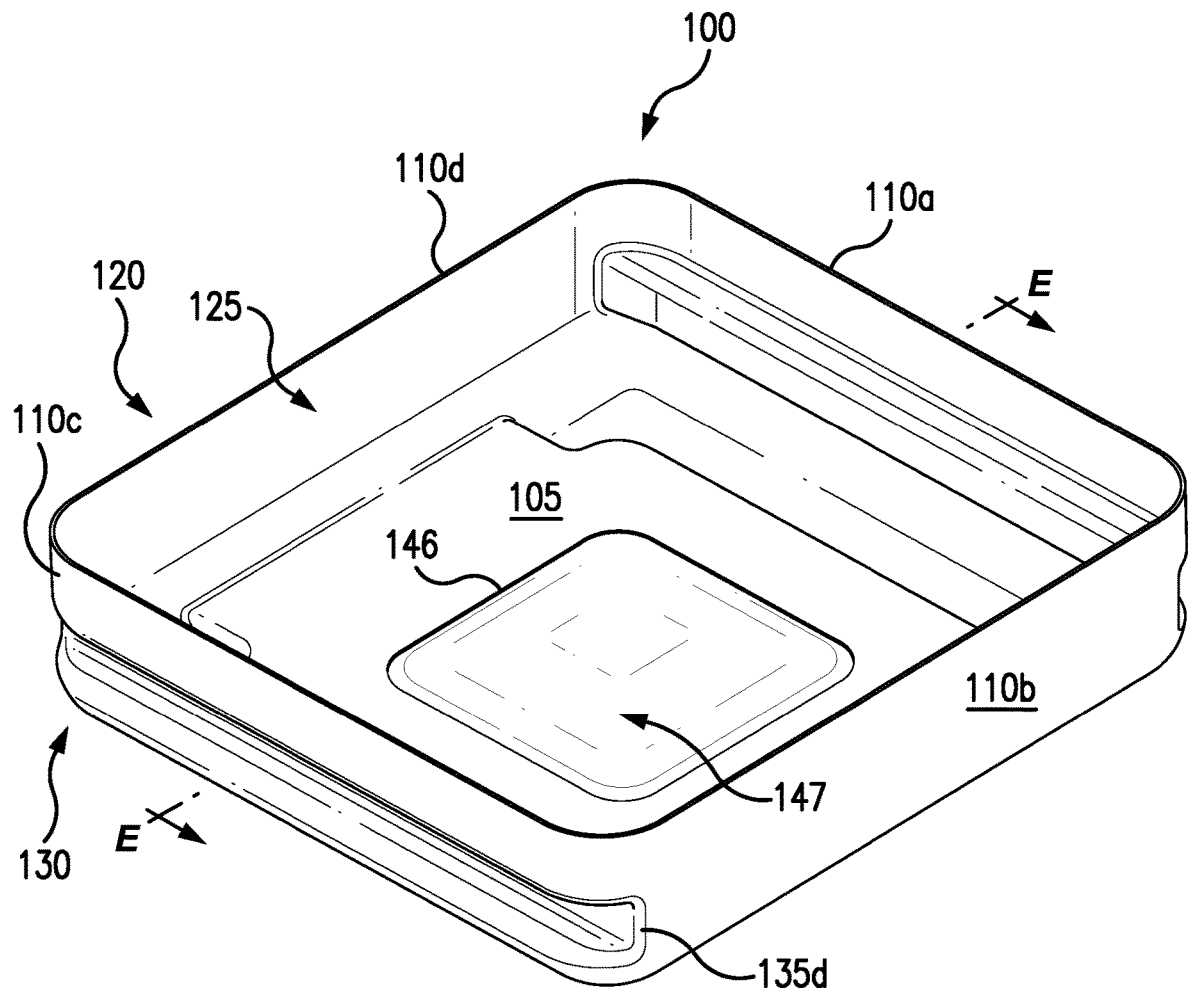
Figure 1F:
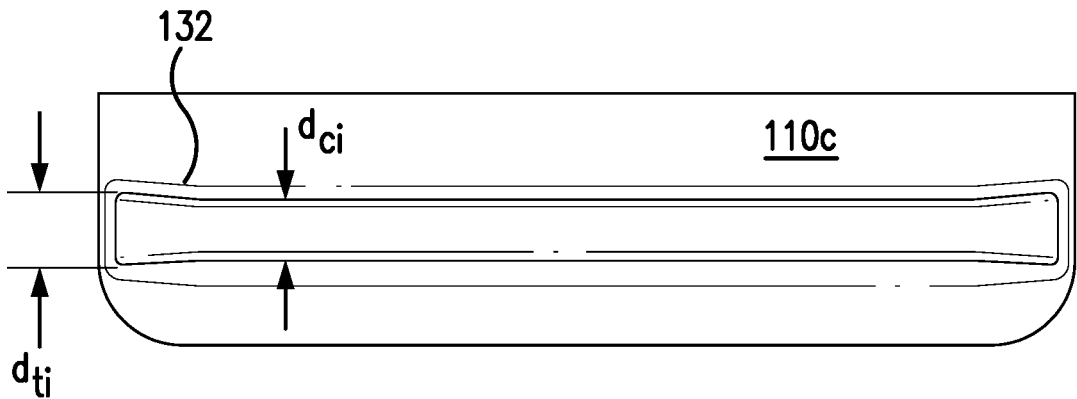
Figure 1G:
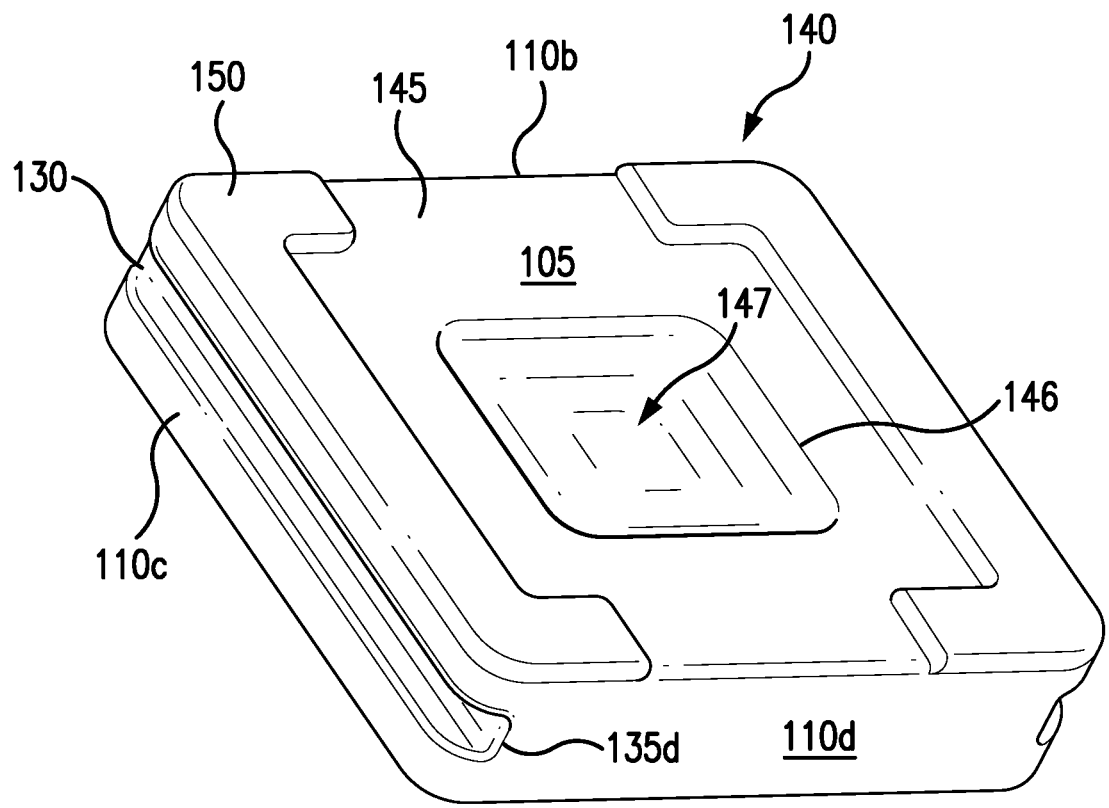
Figure 1H:
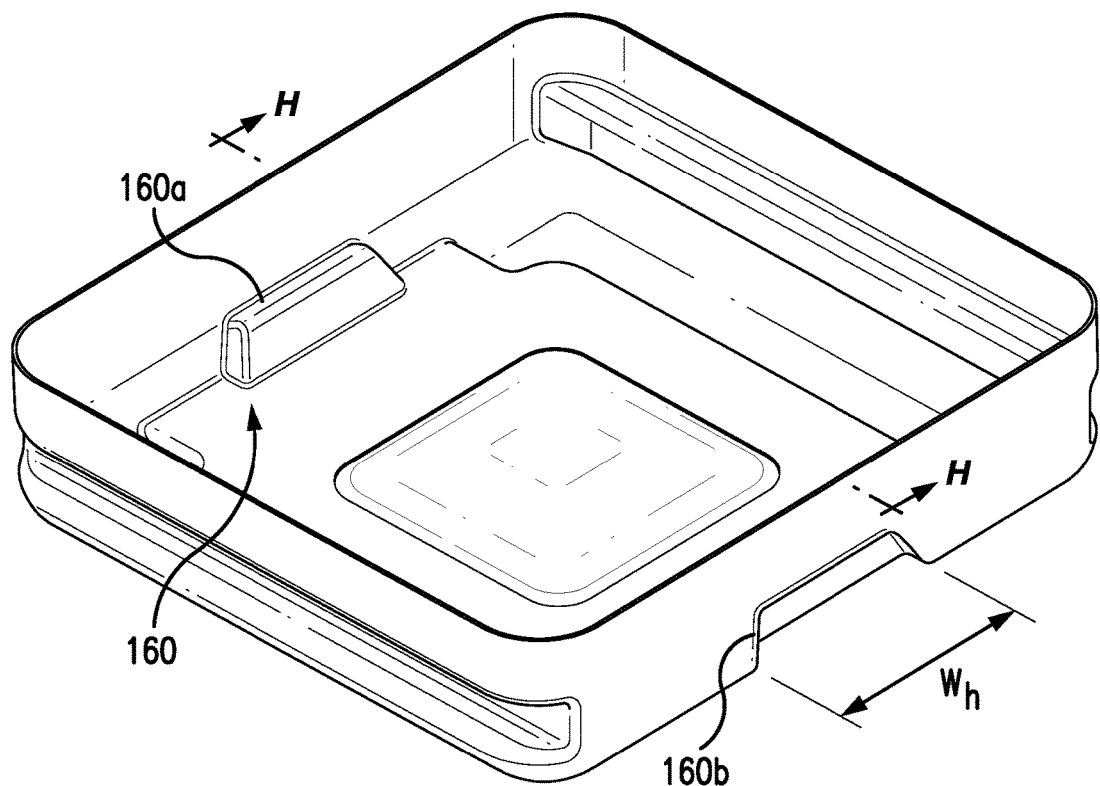
FIGS. 1H-1I illustrate the container of FIGS. 1D-1G with a handle feature in accordance with an embodiment of the present disclosure.
Figure 1I:
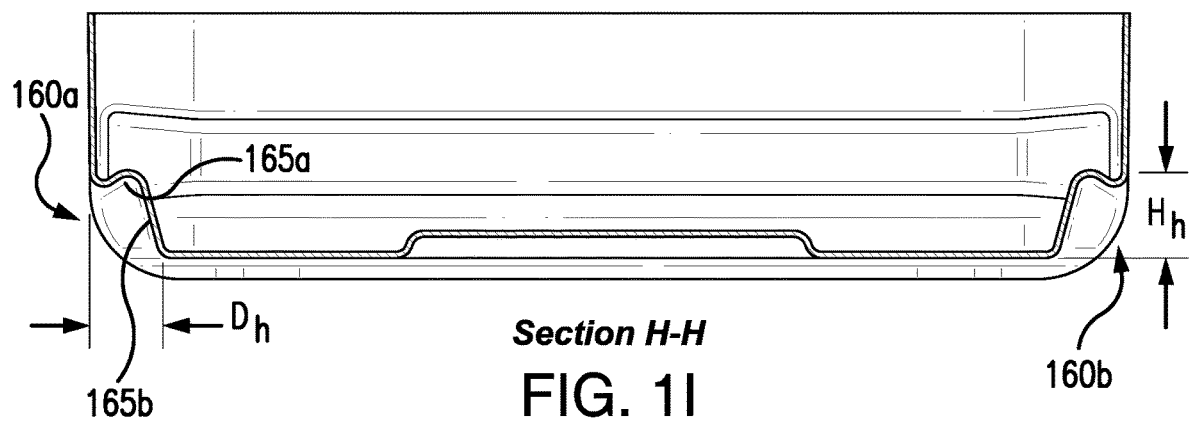

In some embodiments, the central portion 147 of the bottom face 105 may include an indentation 146 that extends from the surface of the recessed portion 145 of the bottom face 105 into the inner portion 125 (e.g., FIGS. 1D-1H, 1J, 1K, 13A-13B and 14A-14B). Referring to FIGS. 1D-1E, indentation 146 may have a square shape and extend into inner portion 125 a distance $d_{RB}$ that may range from about 0 mm. to about 25 mm. As shown, indentation 146 may extend into inner portion 125 a distance $d_{RB}$ of 0.4 in. (10.16 mm). The shape of indentation 146 is depicted as a square, but may be any number of other shapes, such as circular, oval, rectangular, etc. The profile of the indentation 146 may have a plateau-like cross-section, as shown, with a step-up around the edges and a relatively flat portion parallel to the bottom face 105 and recessed portions 145. Alternatively, indentation 146 may have a dome-like cross-section, with a gradual slope from recessed portion 145 of bottom face 105 to an apex at central portion 147, and then a gradual slope back to recessed portion 145. Indentation 146 may encompass outer surface 148 and serve as a space in which the closure feature 610 (e.g., elastic) of liner 600 may gather as it wraps around side faces 110a-110d, and bottom face 105 (see, e.g., FIG. 6B). With the closure feature 610 gathered in indentation 146, the bottom face 105 may be maintained relatively flat, e.g., to facilitate stacking and/or storage. Additionally, or alternatively, the raised surface of the indentation 146 may serve to strengthen the bottom face 105 of the container (e.g., resist twisting or warping), or facilitate manufacturing (e.g., ease removal of the container from an injection or thermoforming mold).

The bottom face 105 and recessed portions 145 may allow for the container 100 to be received in a transportation device in a plurality of orientations. As shown in FIG. 5C, a first container 500a may be receivable into a transportation device 505c via the indentations 130 in a first orientation. The transportation device 505c may be configured such that a container may not be receivable in a lower portion 505 in the first orientation. In some embodiments, the transportation device 505c may lack means for receiving a container by the indentations 130, and/or include additional elements that may otherwise prevent the container 500a from being received, e.g., support elements at a bottom portion of the transportation device 505c. In this event, a second container 500b may be receivable into the transportation device 505c in a second orientation, e.g., rotation of the container 90° about a central axis 155. The recessed portion 145 may allow for the second container 500b to fit in the transportation device 505c with enough vertical clearance from an above first container 500a. In some embodiments, the container 100 may be formed in a rectangle, so that in the second orientation the second container 500b is receivable in a narrower configuration than in the first orientation. It is understood that the first and second containers 500a, 500b may include the features described with respect to the container 100, and/or containers 200a-200e as described below.

In some embodiments, the bottom face 105 and/or surrounding side faces 110a-110d, may incorporate a handle 160, 170, 180 to facilitate holding and movement of the container 100 (see FIGS. 1H-1L, and 13A-13B and 14A-14B, as described further below). Referring to FIGS. 1H-1L, a container 100 with corner handles 160 is depicted. Respective corner handles 160a, 160b may be integrated into opposite sides faces 110b, 110d, and their adjoining recessed portions 145 of bottom face 105. Each handle 160a, 160b, may have a width $W_h$, height $H_h$ and depth $D_h$ dimension that is sized to accommodate the fingers of a user's hand grasping the container palm-side upward. For example, each handle 160a, 160b, may have a width $W_h$ that extends 3-7 in. (76.2-177.8 mm), height $H_h$ that extends 1.0-3.0 in. (25.4-76.2 mm), and depth $D_h$ that extends 0.5-2.0 in. (12.7-50.8 mm). Handles 160a, 160b, may extend inward from respective side faces 110b, 110d into the inner portion 125 of the container 100, and may include a sloped vertical face 165b that transitions to a recessed dimple 165a. Dimple 165a may be sized to accommodate a user's finger tips when grasping the container 100. Other shapes and dimensions of handles 160, 170, 180 may be possible depending on user requirements. Handles 160, 170, 180 may provide a more secure grasping feature compared to holding a container from the bottom face 105 and/or side faces 110a-110d, particularly if the container is encased in a liner 600. For example, the handle 160a, 160b may not extend along an entire length of a side face 110a-110d. Thus, a closure feature 610 may be unable to attach to the dimple 165a and/or sloped vertical face 165b. The liner, cover, or both, may instead extend around to the bottom surface of the container (see FIG. 6B), thereby covering the handles 160, 170, 180. Covering the dimple 165a and the sloped vertical face 165b may reduce or eliminate contamination to the container from a user's hands and/or transportation devices during transport.

Figure 1J:
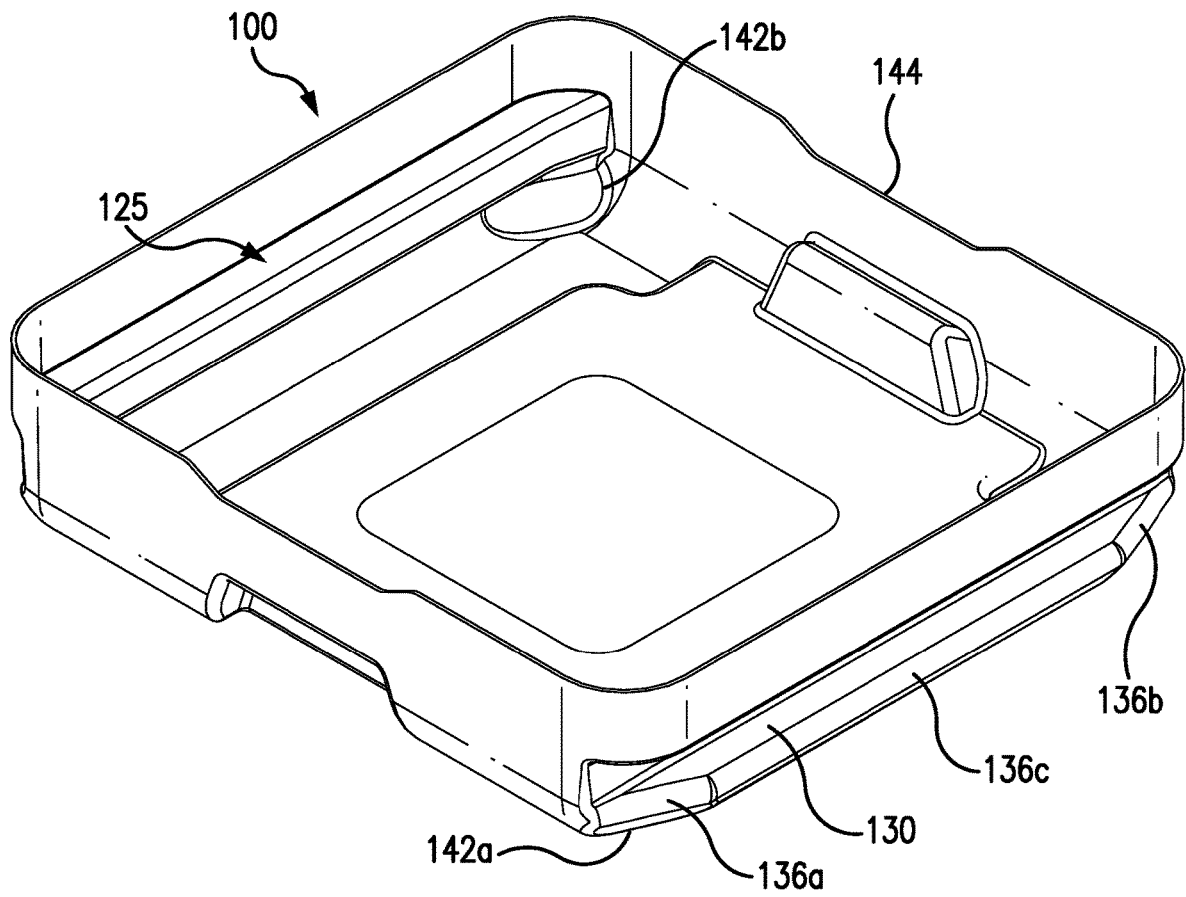
FIGS. 1J-1L illustrate the container of FIGS. 1D-1I with an indentation and contour feature in accordance with embodiments of the present disclosure.

In some embodiments, additional features may be incorporated into the container 100, e.g., to assist a user in locating other features on the container, gripping the container, loading and unloading containers into a transportation device 505a, such as a cart 505c, or to assist in manufacturing. Referring to FIG. 1J, container 100 of FIGS. 1H-1I may include a cut-out 144 on each of the side faces 110b, 110d, where handles 160a, 160b may be located. The slots 144 may be dimensioned to mirror the width of the handles 160. In this regard, the slots 144 can serve several functions for the user. For example, the slots 144 can provide tactile feedback to a user grasping the container from the top as to what sides of the container include the handles and the orientation of the indentations 130. Slots 144 may also provide a more secure gripping surface for users grasping the handles 160 at the bottom of the container 100 with their fingers and the top of the container with their thumbs.

Figure 1K:
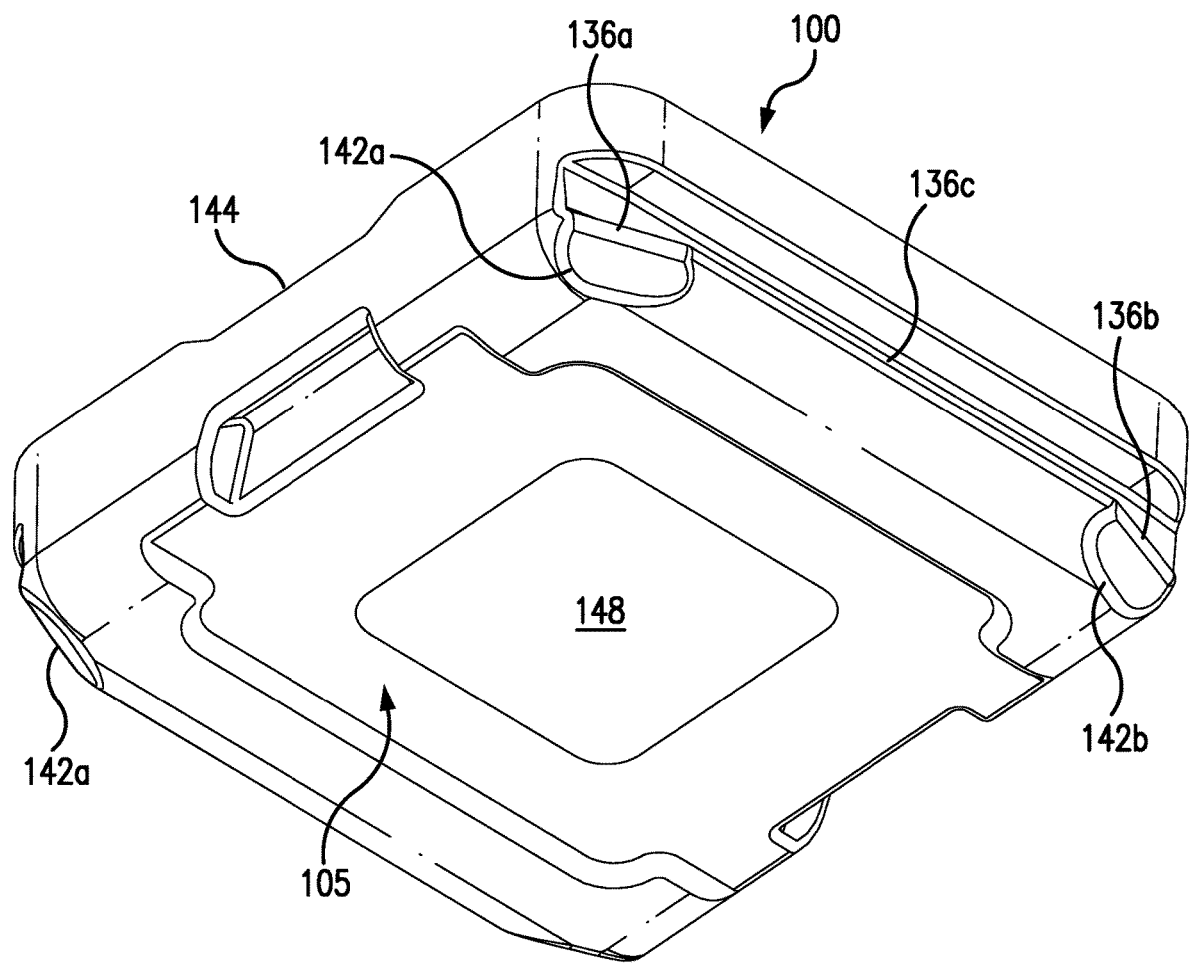
Figure 1L:
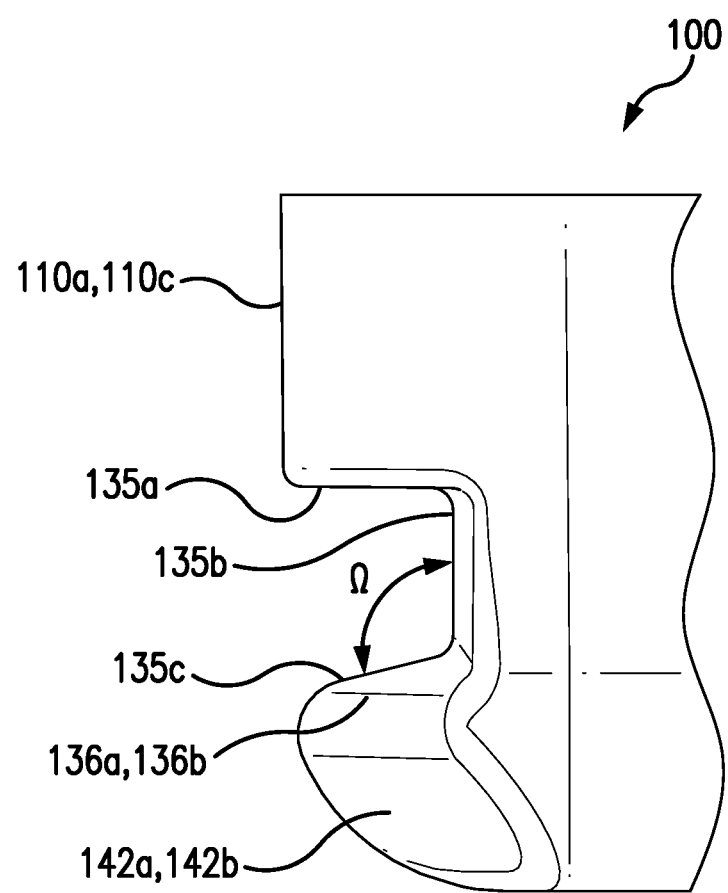

Additional features may also include contouring on the indentations 130, as well as beveling on the rounded edges 107 at the corners of the container underneath the indentations 130. Referring to FIGS. 1J-1L, container 100 may have sloped edges 136a, 136b on the bottom surface 135c, at each end of the indentations 130, on side surfaces 110a, 110c. The sloped edges start at the edge of surface 135c that coincides with the vertical plane of the side surfaces 110a, 110c, and taper along a straight line to the back of the surface 135c, where they join surface 135b at each end of the indentation 130. In between the sloped edges 136a, 136b may be straight edge 136c. The point at which the sloped edges begin at the proximal end and the distal end of the straight edge 136c may vary depending on the desired angle of the slope. In embodiments, the angle of sloped edges 136a, 136b from a vertical plane coincident with straight edge 136c may range from 0-35 degrees, or 10-25 degrees, or 15-20 degrees, or any degree of angle within and including the endpoints of such ranges. Similarly, while sloped edges are illustrated as being straight, they may be configured with a bend or corner as the sloped edges taper, e.g., the point at which a sloped edge begins and ends may define a concave curve or may define two or more straight lines with different slopes, or two or more curves with different radii of curvature, or some combination thereof.

Additionally, or alternatively, side faces 110a, 110c may include beveled surfaces 142a, 142b on the rounded edges 107 underneath the indentations 130, as illustrated in FIGS. 1J-1L. Beveled surface 142a defines a sloped plane with a flat surface extending in a semi-oval from the end of sloped edges 136a, 136b, adjacent edge 136c, to the end of sloped edge 136a, 136b at the back of surface 135c, where surface 135c joins surface 135b at respective ends of the indentation 130. The bottom edge of the semi-oval coincides with and transitions to the portion 150 of the bottom face 105 of the container. The point at which the bottom edge of beveled surfaces 142a, 142b meets and transitions to the portion 150 of the bottom face 105 may vary depending on the desired angle of the sloped plane. In embodiments, the angle of the sloped plane of beveled surfaces 142a, 142b from a horizontal plane coincident with an outer edge of surface 135c (and bottom of sloped edges 136a, 136b, if included) may range from 30-90 degrees, or 40-75 degrees, or 45-60 degrees, or any degree of angle within and including the endpoints of such ranges. While depicted as a flat surface, the sloped plane may have a curved, e.g., concave, surface.

Although container 100 is illustrated in FIGS. 1J and 1K with the ends of each indentation 130 at the corners of the container 100 having sloped edges 136a, 136b, and beveled surfaces 142a, 142b, only sloped edges or only beveled surfaces may be included, and/or sloped edges and/or beveled surfaces may be included on only one end of indentation 130. Sloped edges and beveled surfaces may each extend into the inner portion 125 of the container 100 (FIG. 1J). The beginning and end of the sloped edges and beveled surfaces may coincide (as shown) or they may be different. Including sloped edges and/or beveled surface may facilitate loading of the container in the transportation device or cart. Additionally, softening the corners may facilitate manufacture of the containers. For example, a container configured with sloped edges and/or beveled surfaces may be easier to produce and/or may allow for portions of the container to be strengthened. Injection molding, for example, may be facilitated, as such edges and/or surfaces may allow for the container to be more easily ejected from a mold. As a further example, such edges and/or surfaces may allow for a container with stronger corners when produced by thermoforming (vacuum forming) into a female mold. Sloping the edges and/or beveling the surface may reduce the extent to which a forming material (e.g., plastic) must be stretched down into the mold. That, in turn, may mean that the material in the corners is thicker, resulting in a stronger corner compared to one with a thinner amount of material. Strength of the corner may be important to resist breaking if dropped during use. It is understood that each corner of the container 100 may include contoured features, although some embodiments, may include only one corner, two corners, or three corners, having altered features, and the remaining corners being unaltered.

In some embodiments, the side faces of the container may include a protrusion. Referring now to FIGS. 2A-2E, exemplary embodiments of indentations on containers 200a-200e are illustrated. It is understood that the indentations and protrusions described with respect to FIGS. 2A-2E may be included in the container 100 of FIGS. 1A-1L, and that the indentations and/or protrusions may extend wholly and/or partially around any and/or all of the side faces 110a-110d. Additionally, in some embodiments, the containers 200a-200e may have a contour on the bottom face 105, as shown in container 100, and include indentation 146. In some embodiments, containers 200a-200e may be formed with corner, bottom and/or side handles similar to handles 160, 170, 180 described with respect to container 100.

In FIG. 2A, an indentation 230a may extend inward into the inner portion 125 and may have at least a first surface 255a. The first surface 255a may be positioned substantially parallel to the bottom face 105, so that a profile of the side face 110a-110d may form a substantially perpendicular angle. A second surface 255b may extend from the first surface 255a, e.g., substantially perpendicular to the bottom face 105. In some embodiments, the first and second surfaces 255a, 255b may be similar to the surfaces 135a, 135b described above, and may form an opening "$o_a$". The indentation 230a may be adjacent to a protrusion 240, e.g., extending outward from respective side faces 110a-110d. In some embodiments, the first and/or second surfaces 255a, 255b, may transition to an angled surface 245. The protrusion may further include a straight surface 250, so that a profile of the protrusion 240 is triangular. The straight surface 250 may be positioned substantially parallel to the bottom face 105 and may form a substantially perpendicular angle with respect to the side face 110a-110d.

In some embodiments, an indentation and a protrusion may be formed a distance "d" apart from each other. As shown in FIG. 2B, an indentation 230b may be separate from a protrusion 240. The indentation 230b may be formed substantially similar to the indentation 130, e.g., having substantially perpendicular surfaces 135a-135c formed inwardly into the inner portion 125, a rectangular cross-section to form an opening "$o_b$", tapered end openings 132 or wrap around surface 135d. The protrusion 240 may have an angled surface extending outward from the respective side face 110a-110d and a straight surface 250 to form a substantially perpendicular angle with respect to the side face 110a-110d. The indentation 230b and the protrusion 240 may be separated by distance "$d_b$", e.g., a vertical, or transverse (perpendicular to the bottom face 105), distance on the side face 110a-110d. In some embodiments, a protrusion 240 positioned closer to the bottom face 105 of the container 200b may increase support towards the bottom face 105 for balancing a medical device.

Figure 2C:
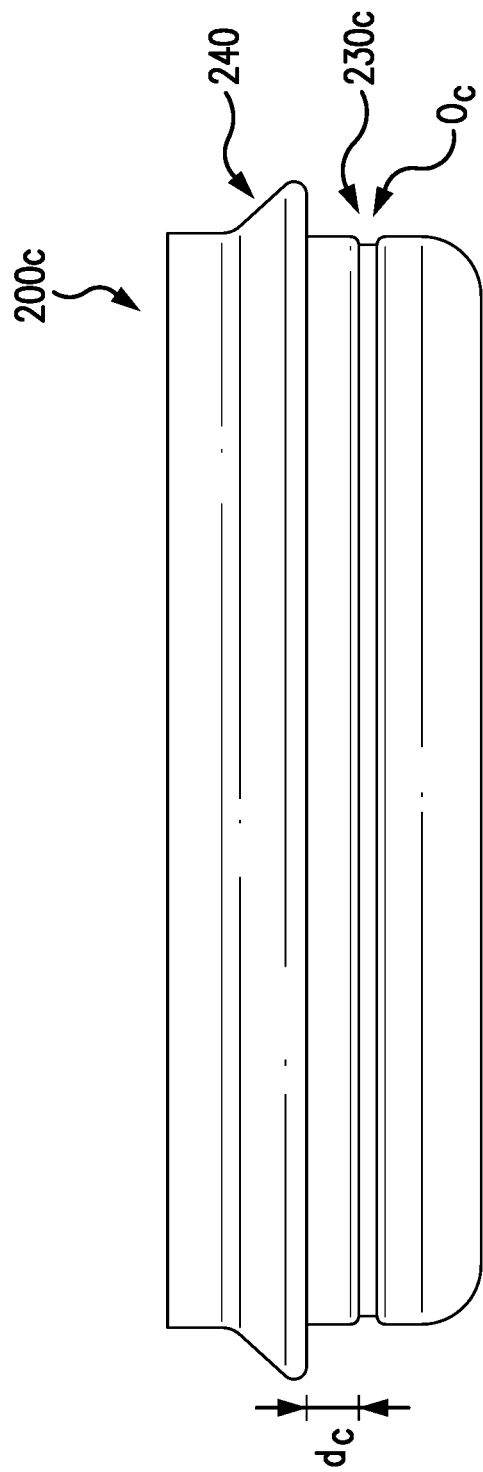

Although FIGS. 2A-2B illustrate embodiments of an indentation being positioned above a protrusion along a side face 110a-110d (e.g., towards the second open-end 120), in some embodiments, an indentation may be positioned below a protrusion (e.g., towards the closed first end 115), as shown in FIG. 2C. The protrusion 240 may be similar to the protrusions described above in FIGS. 2A-2B, having an angled surface 245 and a straight surface 250 so that a profile forms a triangle on the side face 110a-110d. The indentation 230c may be similar to the indentation 230b described above, e.g., having substantially perpendicular surfaces 135a-135c, a rectangular cross-section to form an opening "$o_c$", tapered end openings 132 or wrap around surface 135d. The protrusion 240 and the indentation 230c may be any distance "$d_c$" apart from each other along the side face 110a-110d, e.g., a vertical, or transverse (perpendicular to the bottom face 105) distance.

The protrusion 240 may allow for the containers 200a-200c to be handled, or carried, by a medical professional. For example, the straight surface 250 may be gripped for handling, and may be easily and thoroughly disinfected due to the perpendicularity of the profile in the side face 110a-110d. As described below, the protrusion 230a-230c may be dimensioned so that the respective openings $o_a$, $o_b$, $o_c$ may receive a liner, a cover, or both.

Figure 2D:
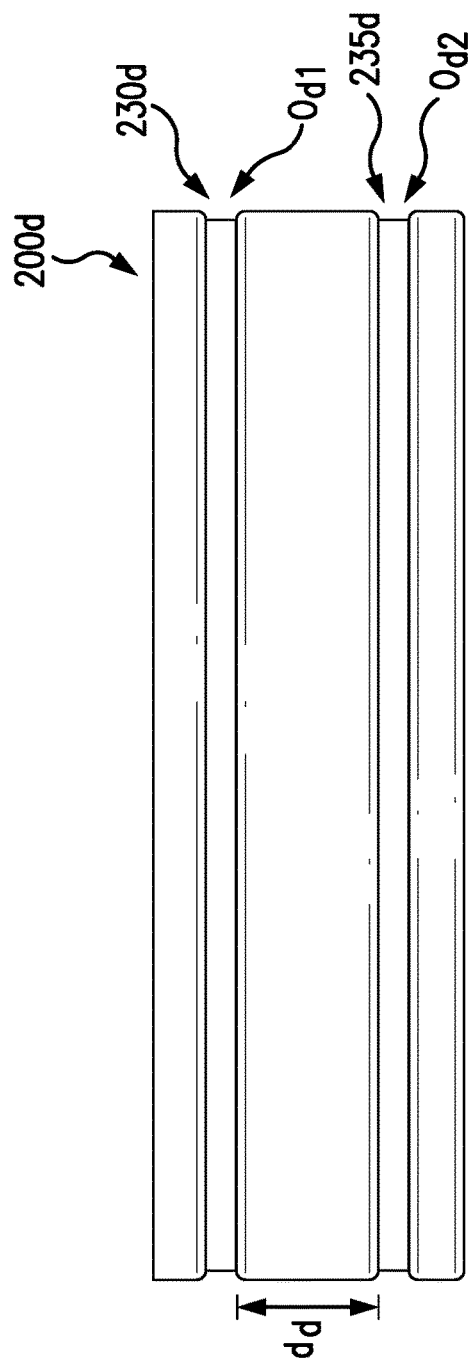

In some embodiments, instead of a protrusion, a second indentation 235d may be included in the container 200d. As shown in FIG. 2D, a side face 110a-110d may include a first indentation 230d, and a second indentation 235d, each formed similarly to indentations 130a, 130b, 230a-230c, as described above, e.g., having substantially perpendicular surfaces 135a-135c, a rectangular cross-section to form respective openings "$o_{d1}$", "$o_{d2}$", tapered end openings 132 or wrap around surface 135d. The first and second indentations 230d, 235d may be positioned any distance "$d_d$" apart from each other along the side face 110a-110d, e.g., a vertical, or transverse (perpendicular to the bottom face 105) distance. The indentations 230d, 235d may be identically formed, or may be sized differently. For example, one of the indentations 230d, 235d may be sized (e.g., having an opening $o_{d1}$, $o_{d2}$) so a medical professional may grip the indentations 230d, 235d for handling, and the other of the indentations 230d, 235d may be sized to receive a liner, a cover, or both.

Figure 2E:
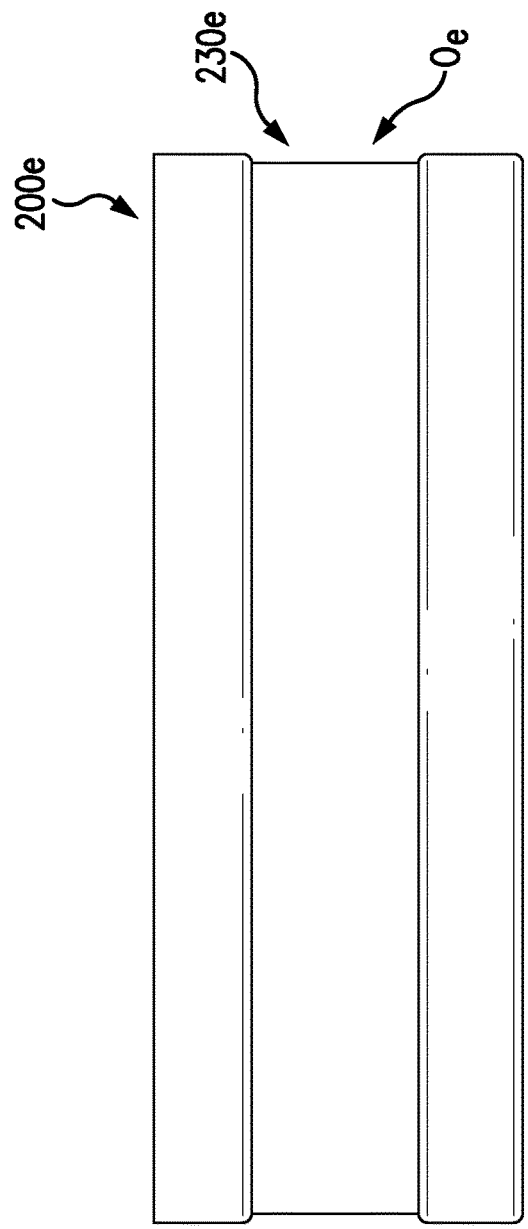
Figure 3A:
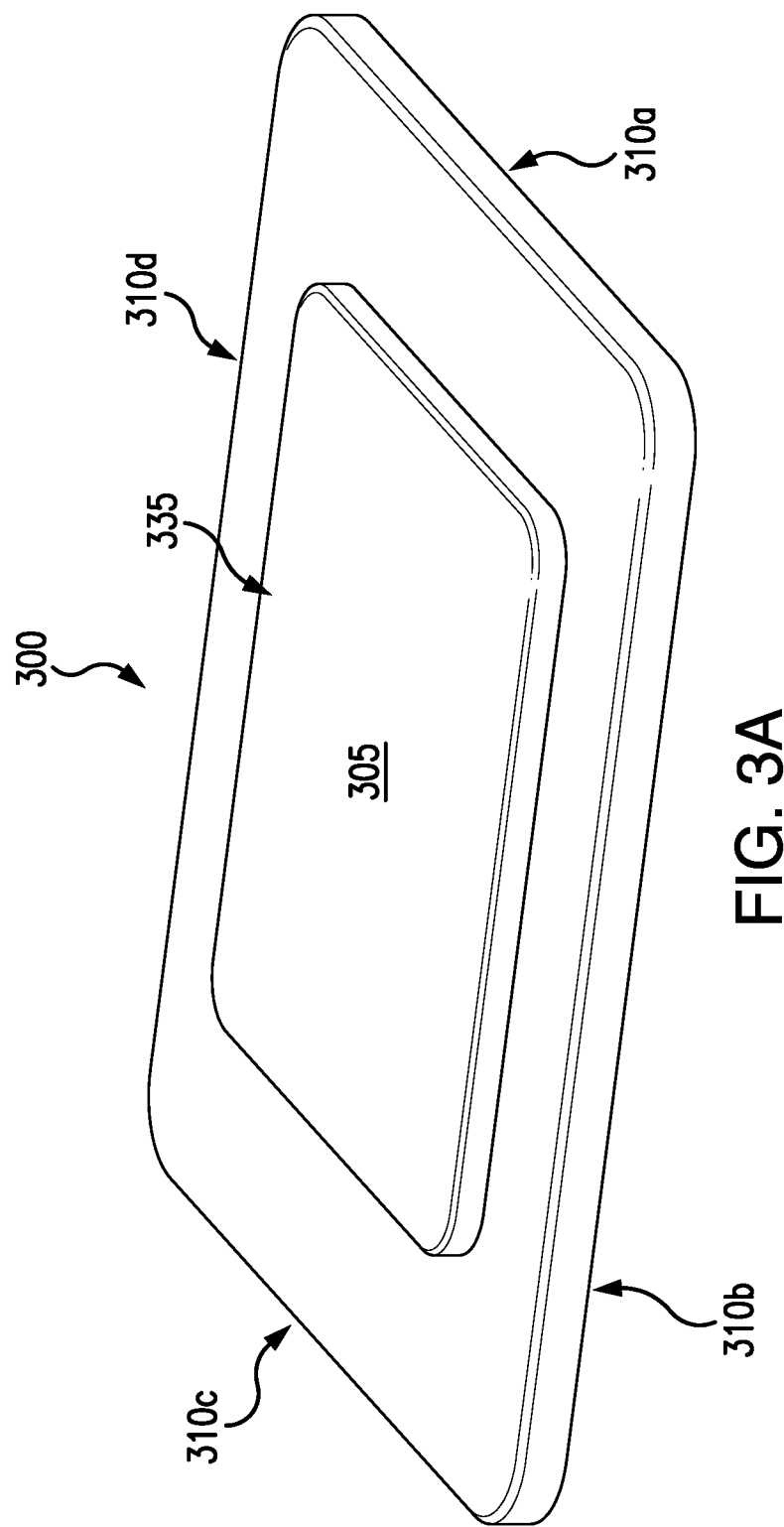
FIGS. 3A-3B illustrate an exemplary embodiment of a lid for a container in accordance with the present disclosure.
Figure 3B:
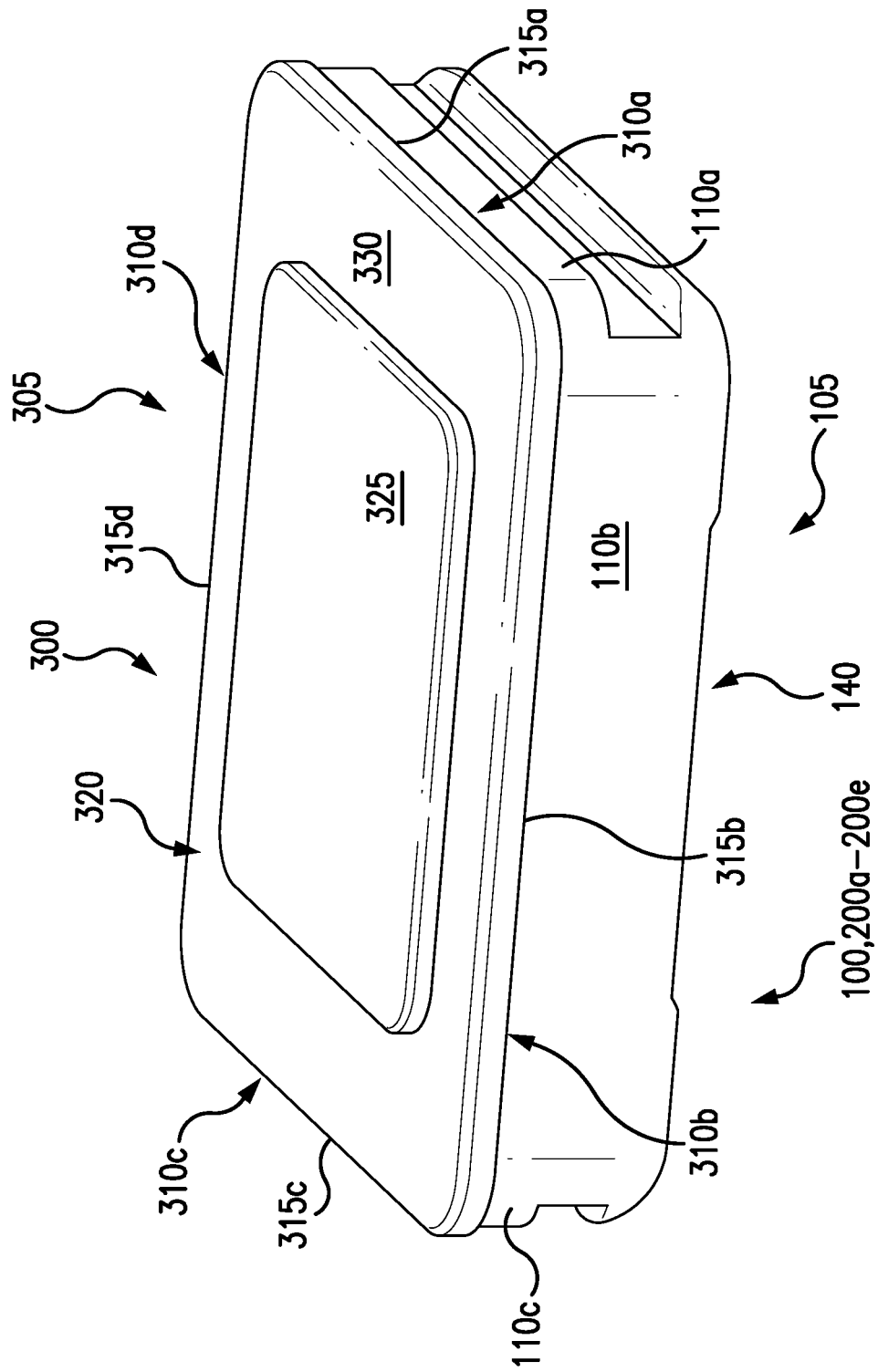

It is understood that the indentations 230a-230e may be sized as desired, e.g., having a greater, or lesser, opening "o". As shown in FIG. 2E, a single indentation 230e may be formed in the side face 110a-110d, having a wider opening "$o_e$" than openings "$o_a$", "$o_b$", "$o_c$", and/or "$o_{d1}$", "$o_{d2}$". The respective openings may be determined by the respective surface 135b, e.g., the surface of the indentation formed substantially perpendicular to the bottom face 105. The opening $o_e$ may allow for a medical professional to grip the indentation for handling the container 200e, and may allow for receiving a cover, a liner, or both, as described below.

In some embodiments, the container 100, 200a-200e may include a lid for covering the second open end 120 and enclosing the inner portion 125. Referring now to FIGS. 3A-3D and 4A-4B, a lid 300 may be shaped to match a container 100, 200a-200e, e.g., to extend over the side faces 110a-110d. The lid 300 may have four sides 310a-310d, e.g., to match the side faces 110a-110d and face 305. Although the lid 300 is shown as rectangular, it is understood that the lid may be any shape to match the shape of the container.

In some embodiments, the lid 300 may include one or more handles. Referring to FIGS. 3C-3D, lid 300 is shown with handles 340a, 340b. Handle 340a may be disposed on side 310b of lid 300 and may be integrated into edge 315b. Handle 340b may be disposed on side 310d of lid 300 and may be integrated into edge 315d. Lid handles 340, in conjunction with container handles 160, 170, 180, may facilitate holding and movement of the container 100 when the lid is attached. Each lid handle 340a, 340b may have a width $W_h$ and depth $D_h$ dimension that matches the width $W_h$ and depth $D_h$ dimension of a corresponding container handle. For example, each lid handle 340a, 340b, may have a width $W_h$ that extends 3-7 in. (76.2-177.8 mm), and a depth $D_h$ that extends 0.5-2.0 in. (12.7-50.8 mm). The slope of lid handle surface 345a may also match the slope of the recessed dimple 165a, such that the two parallel slopes may provide complimentary surfaces for handling. The dimensions and relative slopes may be sized to accommodate the fingers of a user's hand grasping the container palm-side upward in the container handle, while the thumb of the same hand is able to grasp surface 345a of lid handle 340.

As a further example, shown in FIG. 4A, handles 410 may be disposed on the lid 300, 400. One or more handles 410 may extend as protrusions from any and/or all of the sides 310a-310d, edges 315a-315d, and/or overhang 420 of the lid 300, 400, so that a medical professional may handle the lid 300, container 100, 200a-200e, or both. Additionally and/or alternatively, the handles 410 may interface with the rails 515 of a transportation device 505a, 505c so that the container 100, 200a-200e, 500 is received and retained in the transportation device.

The lid 300 may have a face 305 framed by the sides 310a-310d, and may have respective edges 315a-315d extending substantially perpendicular to the face 305. The lid 300 may be removably attachable to the container 100, 200a-200e, so that the edges 315a-315d extend over at least a portion of the respective side faces 110a-110d. When the lid 300 is attached to the container 100, 200a-200e, the face 305 may extend across the second open-end 120 to cover the inner portion 125 and be positioned substantially parallel to the bottom face 105. In some embodiments, the container 100, 200a-200e may be an interference fit into the lid 300, so that the lid may remain in an attached configuration during containment and/or transport to minimize contamination of a medical device. In some embodiments, the lid may have a tolerance so that the container is loosely receivable into the lid.

In some embodiments, a lid 400 may be configured to at least be partially received into the inner portion 125 of the container 100, 200a-200e. As shown in FIGS. 4A-4B, the face 305 may have edges 415a-415d extending substantially perpendicular to the face 305 to extend at least partially into the inner portion 125 of the container 100, 200a-200e. An overhang 420 of the face 305 may extend over and/or contact the edges 415a-415d, so that in an attached configuration the overhang 420 may contact at least a portion of the respective side faces 110a-110d so that the lid 400 encloses the inner portion 125 of the container 100, 200a-200e. In some embodiments, handles 410 may extend from the overhang 420. The edges 415a-415d may be an interference fit into the container 100, 200a-200e, so that the lid may remain attached to the container until as desired by a medical professional.

In some embodiments, the face 305 may include a contour 320, although in other embodiments the face 305 may not include a contour. The contour 320 may be formed as a protrusion, e.g., extending outward relative to the inner portion 125. In embodiments, the contour 320 on the lid 300 may be formed to mate with the contour 140 on the bottom face 105 of the container 100, 200a-200e. The contour 320 may include a raised surface 325 to match the recessed portion 145 in the bottom face 105, and a corresponding portion 330 to match the portion 150 of the bottom face. In embodiments where the recessed portion 145 is in a central portion 147 of the bottom face 105, the raised surface 325 may be positioned in a central portion 335 of the lid 300, so that the raised surface 325 of the face 305 of the lid 300 may be nested into the recessed portion 145 of the bottom face of the container 100, 200a-200e.

In this manner, the lid 300 may be stackable with a container 100, 200a-200e. As shown in FIG. 5B, a first container 500a may be configured to be stacked with a second container 500b, by nesting the lid 300 with the bottom face 105. The first and second containers 500a, 500b may include the features described above with respect to the containers 100, 200a-200e, and may be removably attachable to a lid 300. The nested configuration may allow for the containers to be stacked, e.g., vertically stacked, relative to each other, which may be advantageous for storing extra containers in a medical facility, and/or during transport of a plurality of containers. For example, the nesting configuration may provide stability to the stack of containers to reduce a likelihood of tipping over, which may reduce potential contamination of a medical device. The lid 300, 400 may be formed of a substantially rigid material such as a plastic or composite material, and may be a single-piece thermoformed or molded configuration.

The containment and transportation system may further include a liner for lining the inner portion 125 of the container 100, 200a-200e. In embodiments, a liner may be included so that when a medical device is placed in the inner portion 125 of the container 100, 200a-200e, the liner may act as a protective barrier to the inner portion 125. This may aid in minimizing potential contamination, e.g., when receiving and/or retaining a used medical device. When the medical device is removed for cleaning, the liner may be disposed of so that the container may avoid direct contact with the used medical device.

Figure 6B:
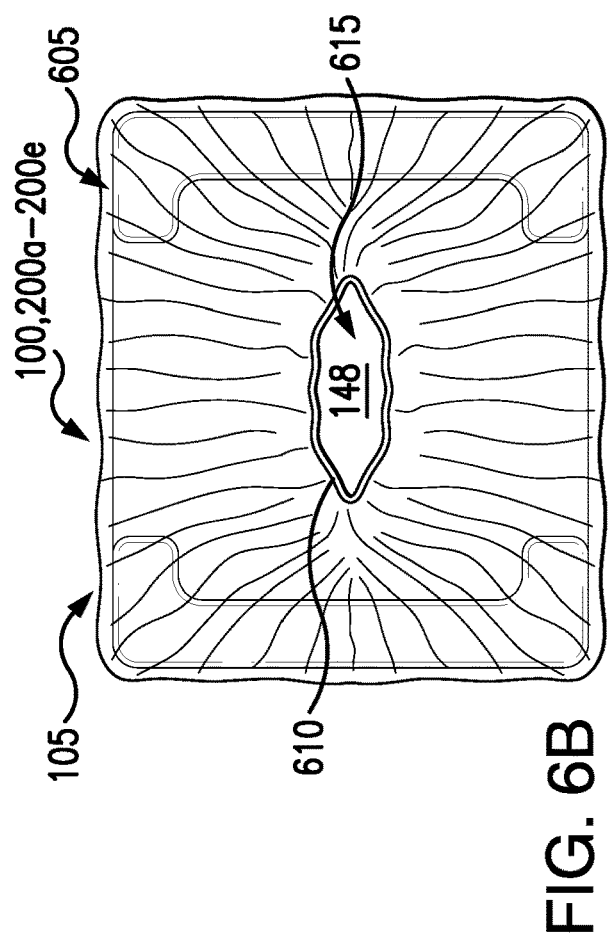
FIG. 6A-6B illustrate an exemplary embodiment of a container liner in accordance with the present disclosure.
Figure 6D:
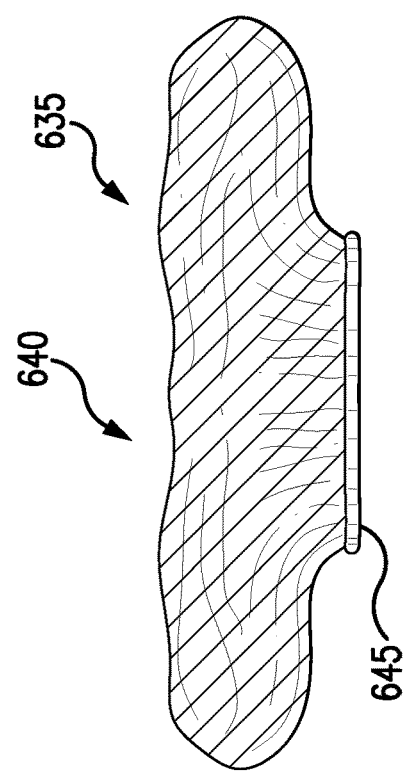
FIGS. 6C-6D illustrate exemplary embodiments of a container cover in accordance with the present disclosure.
Figure 6A:
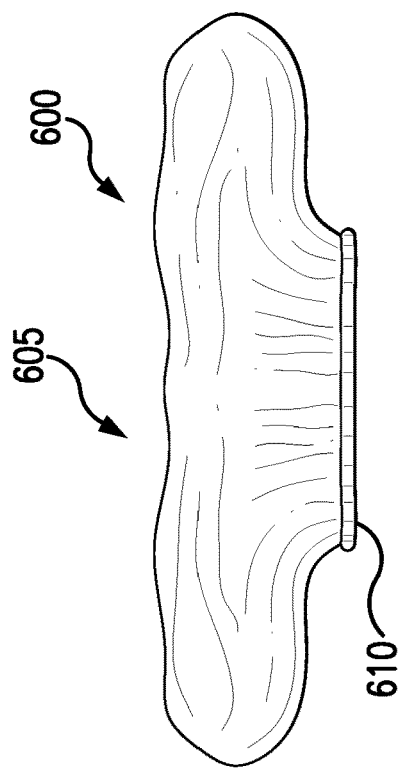

Referring now to FIG. 6A, a liner 600 may have a lining portion 605 and a closure feature 610. The lining portion 605 may be sized to extend over the side faces 110a-110d of the container 100, 200a-200e and line the inner portion 125. The lining portion 605 may be extendable fully over the side faces 110a-110d to an outer surface 148 of the bottom face 105 of the container 100, 200a-200e. The lining portion 605 may enclose, or substantially enclose, the container 100, 200a-200e, to act as a protective barrier and prevent and/or minimize direct contact between a medical device and the container, and/or between a user and the medical device and/or container (see FIG. 7). The lining portion 605 may be formed of a flexible material, such as a single plastic sheet, and may have an edge as a closure feature 610. The flexible material may allow for the liner 600 to be conformable to a profile of the container 100, 200a-200e, e.g., the liner may surround the side faces 110a-110d and may sit in the inner portion 125 of the container. In embodiments, the liner 600 may be at least partially substantially transparent or translucent, although it is also envisioned that the liner 600 may be colored, or opaque. The liner 600 may include symbols, textures, patterns and/or words to, e.g., indicate orientation of the tray within the liner, highlight the closure feature 610, indicate the status of the medical device at various stages of use, reprocessing, transport and handling, or the like.

The liner 600 may be removably attachable to or enclosable about the container by the closure feature 610, so that when the container 100, 200a-200e is lined, the closure feature 610 maintains the liner 600 in position and to enclose the container 100, 200a-200e. As shown in FIG. 6B, when the liner 600 encloses the container 100, 200a-200e, the closure feature 610 may be disposed on the outer surface 148 of the bottom face 105. In embodiments, indentation 146 may be incorporated into the outer surface 148 of the bottom face 105 of container 100, 200a-200e, and the raised space of indentation 146 into the inner portion 125 may accommodate the gathered closure feature 610, e.g., of FIG. 6B, while maintaining a substantially flat bottom face. By aligning the liner 600 so that the lining portion 605 is continuously extended across the inner portion 125 of the container 100, 200a-200e, contamination of the container may be minimized. For example, fluids or other particulates may not leak over the closure feature 610 edge when positioned on the outer surface 148 of the bottom face 105.

In embodiments, the closure feature 610 may be an elastic. The liner 600 may be stretched over the container 100, 200a-200e by the elastic, e.g., so the elastic expands to a stretched position. Once positioned to enclose the container, the elastic may revert to an unstretched position at the outer surface 148 of the bottom face 105. In some embodiments, the elastic may be in an unstretched, gathered position in a substantially oval, or football, shaped opening. As shown in FIG. 6B, the football-shaped opening may leave only a small portion of the outer surface 148 of the bottom face 105 of the container 100, 200a-200e exposed, as indicated by reference numeral 615. By substantially enclosing the container 100, 200a-200e with the liner 600, leaving only a portion of an underside of the container exposed, contamination of the container and/or clean medical device may be minimized. Although an elastic is illustrated in FIGS. 6A-6B, it is understood that the liner may be removably attachable to or enclosable about the container in any manner, including but not limited to a drawstring, adhesive, securement, or combinations thereof (see FIGS. 8A-12B).

In some embodiments, the liner may be extendable partially over the side faces 110a-110d, so that the closure feature 610 remains in a stretched position around the side faces 110a-110d. As described above, the closure feature 610, or elastic, may be engageable with an indentation 230a-230e and/or protrusion 240.

Figure 7:
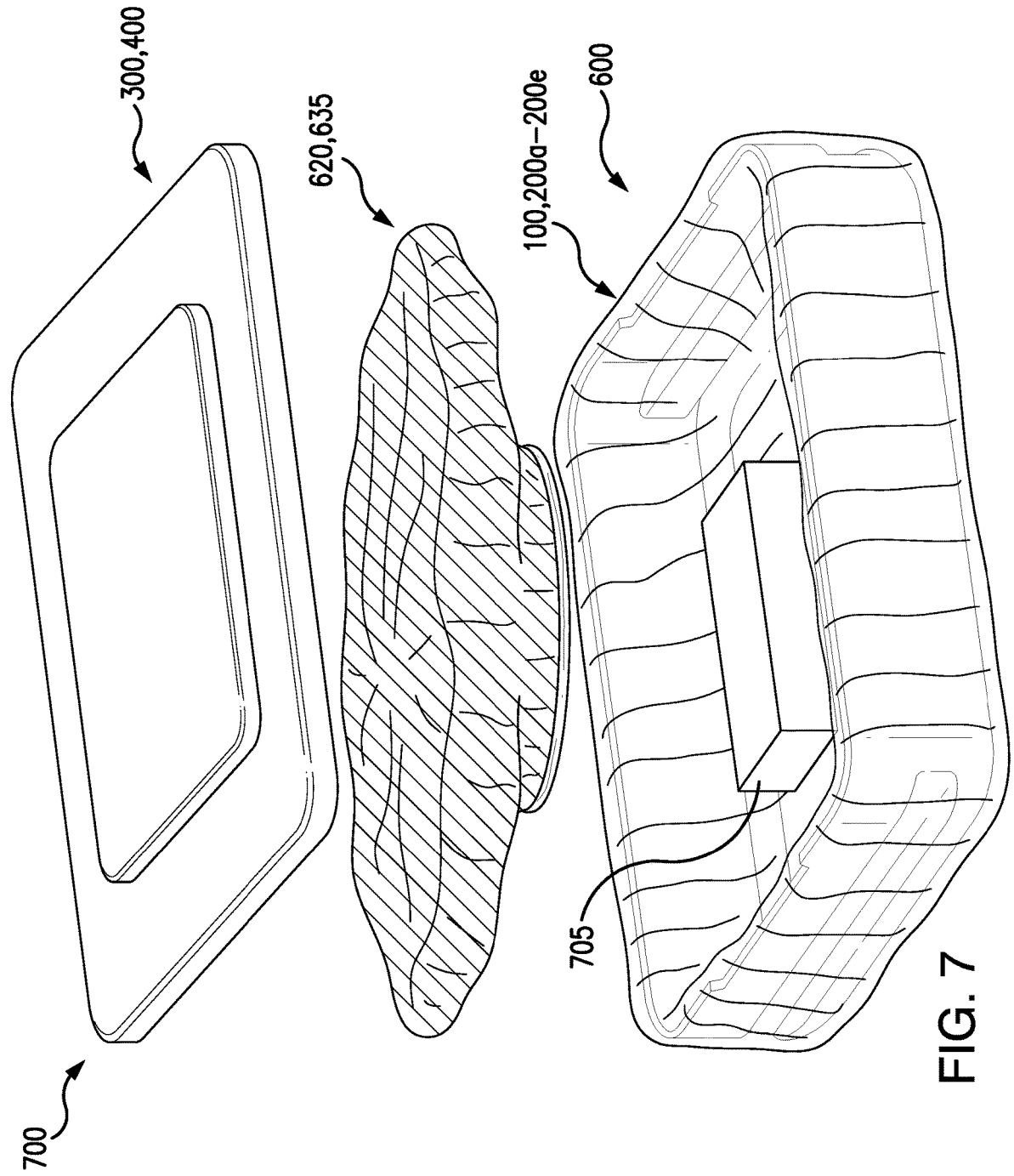
FIG. 7 illustrates an exemplary embodiment of a containment system in accordance with the present disclosure.

As described, the liner 600 may be removably attachable to or enclosable about the container 100, 200a-200e prior to placement of medical device in the inner portion 125 of the container. As shown in FIG. 7, a medical device 705 may be placed in an inner portion 125 of a container 100, 200a-200e after the liner 600 is attached to the container.

Figure 6C:
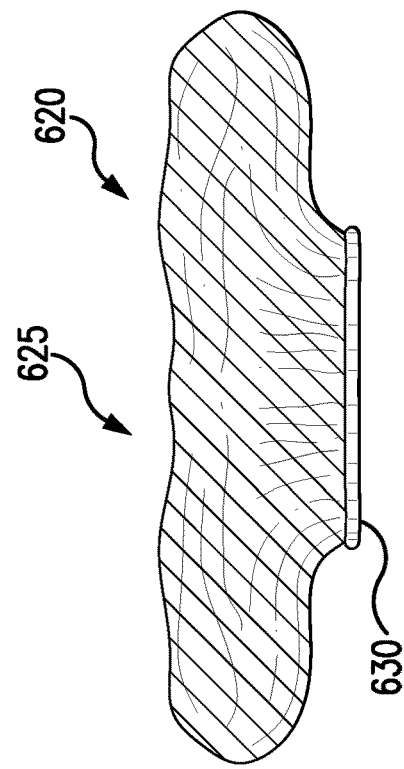

When the medical device is placed in the container, a cover may be extendable across the second open end 120, so that the medical device is captured between the liner 600 and a cover. Referring to FIGS. 6C-6D, and FIG. 7, a first cover 620 may have a cover portion 625 and a closure feature 630, and a second cover 635 may have a cover portion 640 and a closure feature 645. In embodiments, the cover portions 625, 640 may be formed of a flexible material, such as a single plastic sheet, and may have an edge as the respective closure feature 630, 645. The flexible material may allow for the first and second cover 620, 635 to extend across the container 100, 200a-200e, e.g., the first and/or second cover 620, 635 may form a barrier across the second open end 120 of the container 100, 200a-200e. In embodiments, the first and/or second cover 620, 635 may be at least partially substantially transparent or translucent. It is also envisioned that the first and second covers 620, 635 may be different colors, and/or may include symbols, patterns and/or words to indicate the status of the medical device. Different colors and/or patterns may provide an easy indicator for medical professionals traversing through a medical facility, picking up used medical devices and/or delivering clean medical devices, so that incorrect delivery of a medical device is minimized. In embodiments, the liner 600, first cover 620 and/or second cover 635 may include a section for writing on the top surface. Details regarding the medical device may be included by a medical profession, e.g., to document details such as the time the medical device was used, to track a time from use to cleaning. In some medical facilities, a used medical device must be reprocessed within a predetermined time period, such as less than 1 hour. In embodiments, the first cover 620 may be different than the second cover 635, so that a medical professional may have a visual indication of a condition of the medical device 705 in the container 100, 200a-200e. For example, a green colored cover 620 may indicate a clean medical device. A medical professional may be able see the green cover 620 and transport the medical device to a patient procedure location for use. Similarly, a red colored cover 635 may indicate a used medical device, so the medical professional may transport the medical device to a reprocessing location. In some embodiments, a hazardous waste symbol, and/or a pattern of hazardous waste symbols, may be printed on a cover 635 to indicate a used medical device, so that the pattern may indicate to a medical professional for proper handling and disposal.

The first and/or second covers 620, 635 may be removably attachable to or enclosable about the container by the respective closure feature 630, 645, so that the covers 620, 635 are substantially taut (e.g., the covers may not sag into the inner portion 125 of the container) across the second open end 120. The first and/or second covers 620, 635 may be exchangeable with each other, e.g., by the medical professional. For example, after endoscope reprocessing, a clean medical device 705 may be placed in a lined container (see FIG. 7), and a first cover 620 may be extended across the second open end 120, which may be green in color. The container may be transported from a reprocessing location to a medical procedure location, where the clean medical device may be used on a patient. Subsequent to the procedure, the used medical device may be placed back in the container, and a second cover 635 may be extended across the second open end 120, which may be red in color. This may indicate to a medical professional, or other medical facility personnel that the medical device should be transported back to the reprocessing area for cleaning. Alternatively, the first cover may be reversible, as opposed to having a second cover, with each side of the reversible cover for visual verification of a different condition of the medical device. For example, after endoscope reprocessing, a clean medical device 705 may be placed in a lined container (see FIG. 7), and a reversible cover 620 with opposing sides that are green and red may be extended across the second open end 120, with the green side facing upwards providing a visual verification of the clean condition of the endoscope. The container may be transported from a reprocessing location to a medical procedure location, where the clean medical device may be used on a patient. Subsequent to the procedure, the used medical device may be placed back in the container, and the reversible cover 620 may be extended across the second open end 120, with the red side facing upwards providing a visual verification of the used condition of the endoscope. This may indicate to a medical professional, or other medical facility personnel that the medical device should be transported back to the reprocessing area for cleaning. Similarly, opposing sides of a reversible cover may include symbols, patterns and/or words to indicate the status of the medical device at various stages of use, reprocessing, transport and handling.

Similar to the liner 600, the first and/or second cover 620, 635 may enclose the side faces 110a-110d, as well as the already-attached liner 600, and closure features 610 may be disposed on the outer surface 148 of the bottom face 105. In embodiments, indentation 146 may incorporated into bottom face 105, as described and the raised space into the inner portion 125 may accommodate the gathered closure features 610 of the first and/or second cover 620, 635, similarly to closure feature 610 of liner 600, shown in FIG. 6B, while maintaining a substantially flat bottom face. By aligning the first and second covers 620, 635 so that the cover portions 625, 640 may be continuously extended across the inner portion 125 of the container 100, 200a-200e, a clean medical device may be protected from outside contamination. Additionally, a used medical device, which may include contaminants from a patient, may be containable by the cover 620, 635, and the liner 600. For example, fluids or other particulates may not leak over the closure feature 630, 645 when positioned on the outer surface 148 of the bottom face 105.

In embodiments, the closure feature 630, 645 may be an elastic. The covers 620, 635 may be stretched over the container 100, 200a-200e by the elastic, e.g., so the elastic expands to a stretched position. Once positioned to enclose the container, the elastic may revert to an unstretched, gathered position at the outer surface 148 of the bottom face 105. In some embodiments, the first and/or second covers 620, 635 may partially enclose the side faces 110a-110d so that closure features 630, 645 may engage with indentations 230a-230e and/or protrusions 240, to remain in a substantially stretched position. In some embodiments, the elastic may be in an unstretched position in a substantially oval, or football, shaped opening. Similar to the liner 600, the football-shaped opening may leave only a small portion of the outer surface 148 of the bottom face 105 of the container 100, 200a-200e exposed (see FIG. 6B). By substantially enclosing the container 100, 200a-200e with the covers 620, 635, leaving only a portion of an underside of the container exposed, contamination of the container and/or clean medical device may be minimized. Although an elastic is illustrated in FIGS. 6C-6D, it is understood that the first and/or second covers may be removably attachable to or enclosable about the container in any manner, including but not limited to a drawstring, adhesive, securement, or combinations thereof (see FIGS. 8A-12B).

In embodiments, liner 600, and/or first and/or second covers 620, 635, may incorporate an elastic configuration for respective closure features 610, 630, 645, such that once liner 600, and/or first and/or second covers 620, 635, are positioned to enclose the container the elastic configuration of the respective closure features 610, 630, 645 assumes a partially stretched position at the outer surface 148 of the bottom face 105 and leaves an exposed portion 615 of the outer surface 148 of the bottom face 105 of the container 100, 200a-200e that is larger compared to portion 615 in FIG. 6B. By substantially enclosing the container 100, 200a-200e with the liner 600 and covers 620, 635, including a perimeter portion of the underside of the container, contamination of the container and/or clean medical device may still be minimized, and the container may still be protected against a user's fingers contacting the bottom face of the container around the perimeter of the container where the container may be typically grasped when handling it.

Figure 6E:
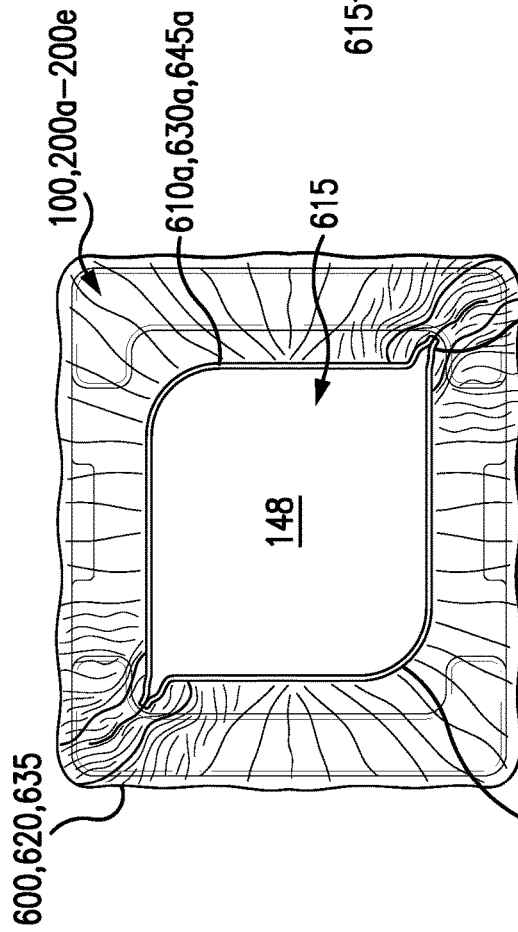
FIGS. 6E-6H illustrate exemplary embodiments of a container liner and cover in accordance with the present disclosure.

Referring to FIG. 6E, an embodiment of an elastic is illustrated, which may be employed interchangeably as the closure feature 610 or the liner 600, and/or the respective closure features 630, 645 of first and second covers 620, 635.

As a liner 600, the lining portion 605 may be sized to extend over the side faces 110a-110d of the container 100, 200a-200e and line the inner portion 125. The lining portion 605 may be formed of a flexible material, such as a single plastic sheet, and may have an elastic at an edge of the liner 600 as the closure feature 610. The flexible material may allow for the liner 600 to be conformable to a profile of the container 100, 200a-200e, e.g., the liner may surround the side faces 110a-110d and may sit in the inner portion 125 of the container. As a cover 620, 635, cover portions 625, 640 (FIGS. 6C-6D) may be formed of a flexible material, such as a single plastic sheet, and may have an elastic at an edge of the first cover and second cover, as the respective closure feature 630, 645. The flexible material may allow for the first and second cover 620, 635 to extend tautly across the container 100, 200a-200e, e.g., the first and/or second cover 620, 635 may form a barrier across the second open end 120 of the container 100, 200a-200e.

The liner 600 and first and/or second covers 620, 635 may be removably enclosable about the container by the respective closure feature 610, 630, 645. As illustrated in FIG. 6E, when enclosing the container 100, 200a-200e, the closure features 610, 630, 645 may be disposed on the outer surface 148 of the bottom face 105. The closure feature 610, 630, 645 may be an elastic comprising a first elastic piece 610a, 630a, 645a and a second elastic piece 610b, 630b, 645b. The two elastic pieces may be connected to each other at junctions 610c, 630c, 645c, at terminal ends of the pieces to form a continuous elastic at the edge of the liner or cover. Connections at junctions 610c, 630c, 645c may formed by sewing, welding, adhesive, mechanical fasteners, and the like. While two junctions are described, it is envisioned that any number of junctions and pieces of elastic may be implemented.

Figure 6F:
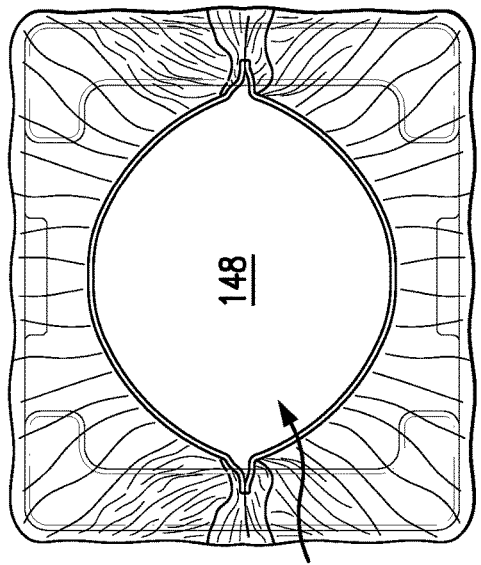
Figure 6G:
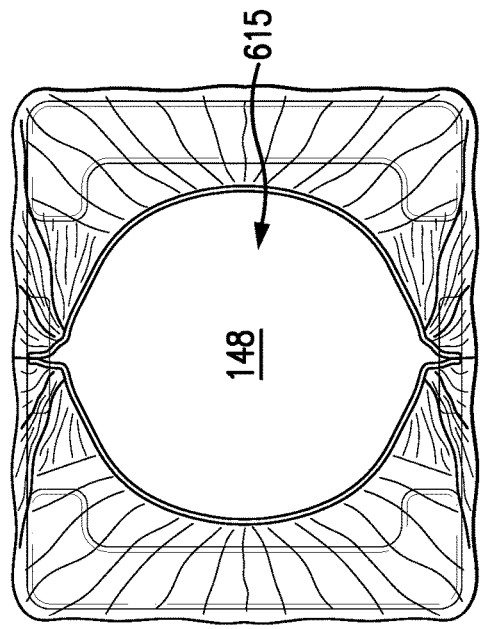

The elastic and the flexible material of the liner and the covers may be gathered in a pinched position at the junctions at the ends of the two pieces of elastic, resulting in an excess of material gathered nearer to and at the junctions, compared to material farther from and midway between the junctions. The material may be pleated, such that when packaged and before being deployed about a container, the liner and covers may be folded, e.g., accordion-style, into a compact form. The number, type and/or location of the junctions, the amount of gathering of material at the junctions, and/or maintaining the elastic in a partially stretched position at the perimeter of the bottom face, may allow for control over a variety of different shapes and sizes of exposed portions 615 of the outer surface 148. As examples, with reference to FIGS. 6E, 6F, and 6G, exposed portions 615 in the shape of a square opening with junctions at the corners of the container (FIG. 6E), a football-shaped opening (FIG. 6F) with junctions along the side faces of the container having the indentations 130, and an oval or circular opening (FIG. 6G) with junctions along the side faces of the container having the handle 160.

Figure 6H:
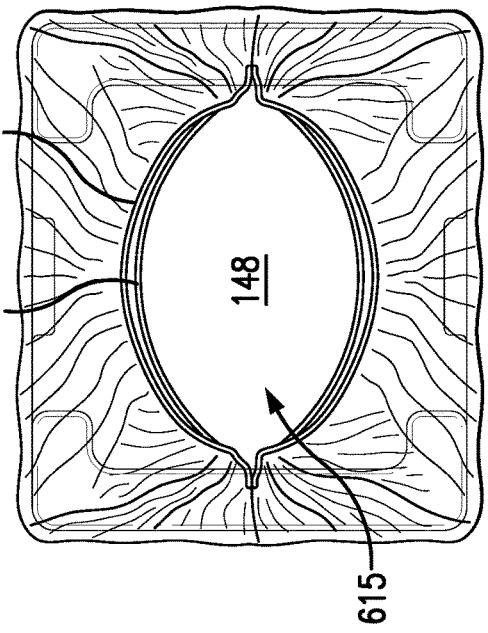

Referring to FIG. 6H, an example of the first cover 620 or second cover 635 having a two-piece elastic configuration is illustrated, enclosing the side faces 110a-110d of the container, as well as enclosing the liner 600 having a two-piece elastic configuration, with the closure features 610 and 630 or 645 disposed on the perimeter portion of the outer surface 148 of the bottom face 105.

The covers 620, 635 may be removably attachable to or enclosable about the container 100, 200a-200e and the attached liner 600. FIG. 7 illustrates an exploded view of an exemplary embodiment of a containment and transportation system 700, including a medical device 705 enclosable between the respective cover 620, 635 and the liner 600, thereby avoiding direct contact with the container. In embodiments, the lid 300, 400 may be closed over the first or second cover 620, 635, which may provide additional protection to a clean medical device, and/or containment of contaminants of a used medical device. The respective cover portions 625, 640 may have excess material such that when a lid 300, 400 is closed onto the container 100, 200a-200e, the first and/or second cover 620, 635 may not be damaged or otherwise ripped or torn. Minimization or prevention of tearing may protect contamination of the container or lid from a used medical device, and/or may protect a clean medical device from outside contaminants. Similarly, the liner 600, the first cover 620, and/or the second cover 635 may have excess material for coverage in the indentations 130, 230a-230e and/or protrusions 240, so that when a container is inserted and/or removed from a transportation device the liner 600, first cover 620, and/or second cover 635 may not be damaged or otherwise ripped or torn, while still fitting to the container 100, 200a-200e as described.

Figure 5D:
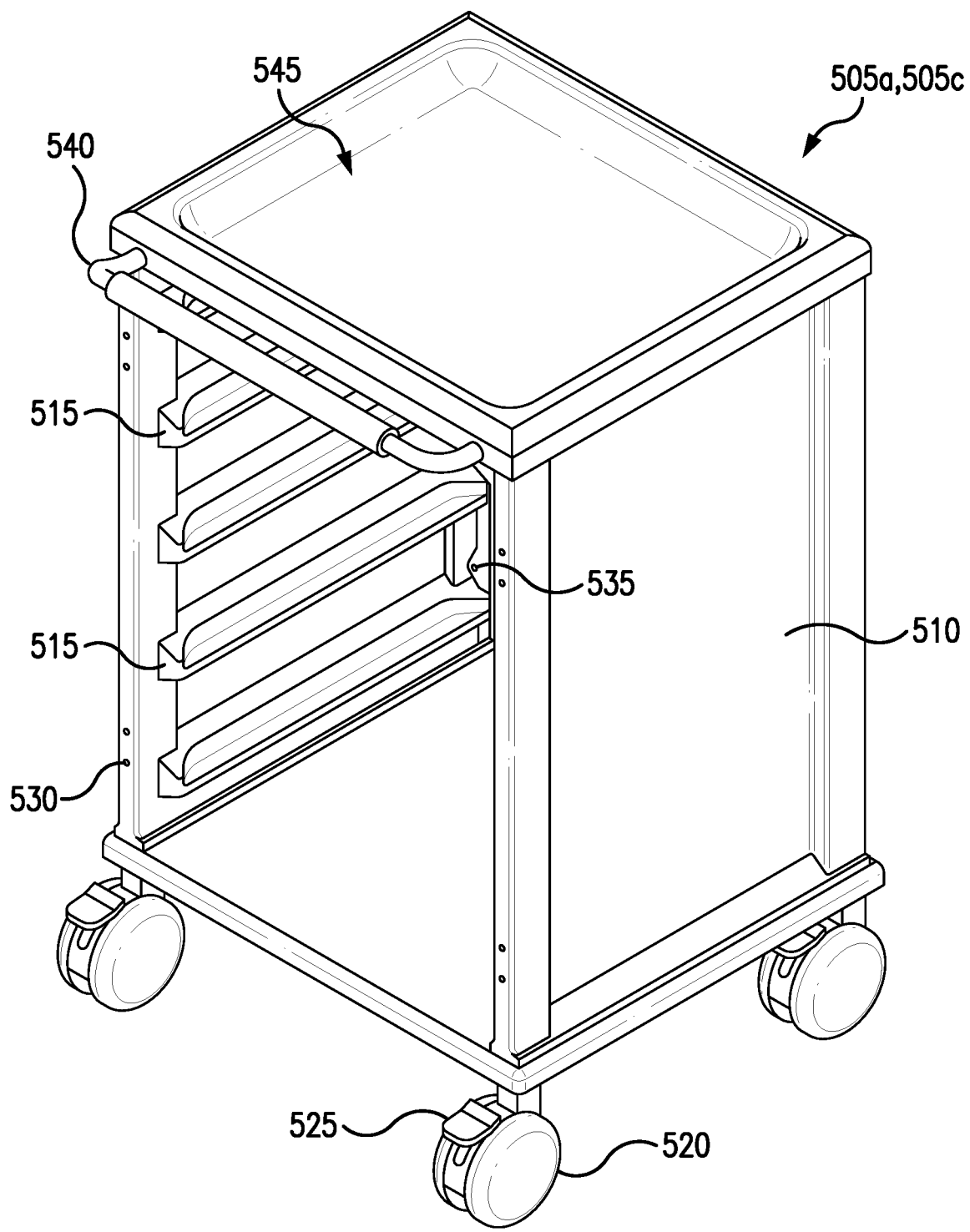
Figure 5E:
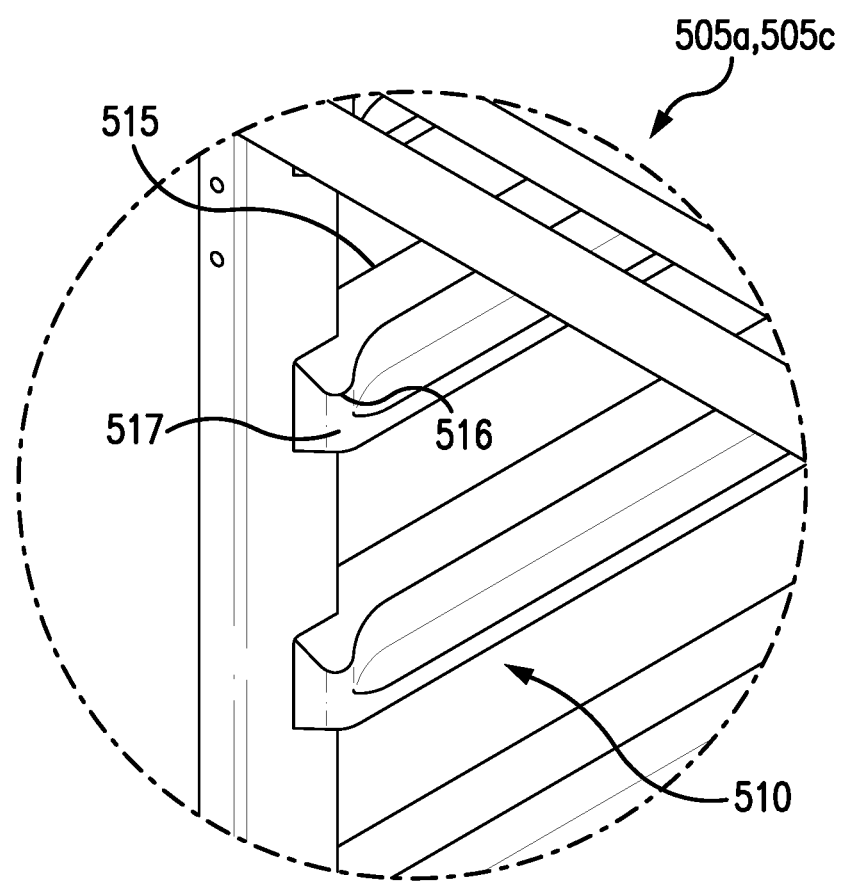
FIG. 5E illustrates an exemplary embodiment of a rail configuration for a containment system in accordance with the present disclosure.

As shown in FIG. 5A, and FIGS. 5C-5D, a transportation device 505a may include sides 510, for receiving one or more containers 100, 200a-200e therebetween. In some embodiments, the transportation device 505a may be a cart 505c. The sides 510 may include rails 515 for engaging with the indentations 130, 230a-230e, and/or protrusions 240 of the container 100, 200a-200e. The rails 515 may be spaced a distance apart so the transportation device 505a may receive a plurality of containers and in parallel pairs so the containers may remain substantially parallel to the ground. Referring to FIG. 5D, in some embodiments, the transport device 505a, or cart 505c, may be a rolling cabinet with sides 510 and rails 515 for holding multiple containers 100, 200a-200e. With reference to FIG. 5E, in some embodiments, rails 515 for the sides 510 of the transport device 505a, or cart 505c, may include a softened (e.g., rounded) top and bottom horizontal surface edge 516, and/or softened (e.g., rounded) vertical surface edge 517, at the end of the rails 515 that comprises the opening of the transport device 505a, or cart 505c. Such softened horizontal and/or vertical surface edges 516, 517 may be incorporated into the rails 515 to facilitate loading of container 100, 200a-200e, into the transport device or cart, e.g., edges 516, 517 may present a surface to engage the indentations 130 of the containers that is softer than a straight horizontal and/or vertical edge, which may be prone to catching on the indentation or catching on a liner and/or cover that may be extended over the indentations. The cart may include handle 540 and casters 520 with individual locking tabs 525. The cart is shown with four casters, but a greater or lesser number of casters may be possible, as well as other means of transporting the cart other than casters. The cart may accommodate a door (not shown), which may be hung off hinges secured to holes 530 on either side of the cart 505c. The choice of which side of the cart is chosen for mounting the door dictates in which direction the door will swing when opened. A latch for the door may be secured to the cart with holes 535. In some embodiments, the top of the cart may be formed with an indentation or depression 545, which may be used to securely hold a container 100 against sliding when a user is accessing the contents of the container. The indentation 545 may also be used for the purpose of stacking cabinets on top of one another. For example, if the casters are made to be removable and the base of each cabinet is formed with a raised surface that extends toward the floor and matches the contour of the indentation 545, one cart can be stacked on top of another cart. This may be done for efficiency in storage or to increase the number of containers that may be transported at one time.

As described above, in some embodiments the liner 600, first cover 620, and/or the second cover 635 may be extendable to enclose the side faces 110a-110e, so that the indentations and/or protrusions are also enclosed. The liner 600, first cover 620, and/or second cover 635 may act as a protective barrier from the transportation device 505a, 505c to prevent contamination of a clean medical device and/or to limit transfer of contaminants of a used medical device between the container and the transportation device.

Figure 8A:
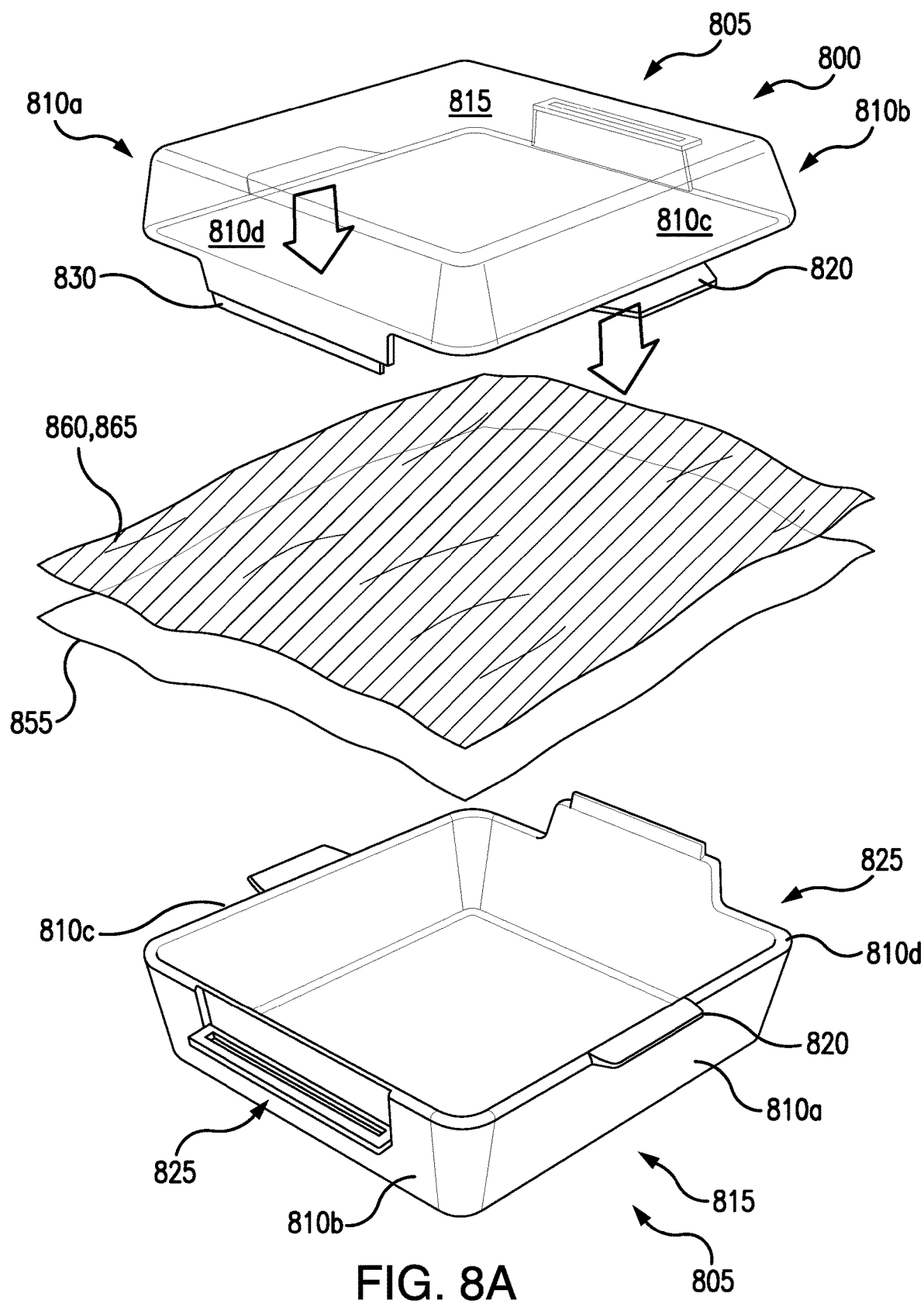

According to exemplary embodiments of the present disclosure, a containment system 800 may include a combination container and lid 805, as illustrated in FIGS. 8A-8C. For example, the container and lid may be a single configuration and interchangeable with each other, so that separate components are not needed for the containment system, and may be compatible with a plurality of transportation devices. The container and lid 805 may have side faces 810a-810d and a bottom face 815 to form an inner portion 825. The container and lid 805 may have four sides to form a rectangle or square, but it is understood that any number "n" of sides may be included to form any shape for containment and transportation of a medical device.

The container and lid 805 may have one or more handles 820 formed as protrusions from the side faces 810a-810d from the container and the lid. The handles 820 may be disposed centrally along a side face 810a-810d, so that the container and lid 805 may be balanced during handling. Additionally, the handles 820 may engage with a transportation device, e.g., rails of transportation device 505a, 505c, to be receivable and retainable in the transportation device for transport throughout a medical facility as desired. Since the lid and container 805 are identical, when configured together to enclose a medical device, the handles 820 may align with each other on the respective side faces 810a-810d.

In embodiments, the lid and container 805 may include a locking feature 825 and a lockable feature 830, disposed on one or more side faces 810a-810d. For example, a locking feature 825 may be disposed on a side face 810b of the lid and container 805, and a lockable feature 830 may be disposed on opposing side face 810d of the lid and container 805, so that in an attached configuration, a lid 805 may be flipped upside down from a position of the container 805 and rotated 180° to engage the locking feature 825 on the container 805 and the lockable feature 830 on the lid 805.

The lid and container may be removably attachable with each other, to engage by the locking feature 825 and the lockable feature 830. The locking feature 825 and the lockable feature 830 may include mating tabs and/or slots for engagement. For example, the locking feature 825 may include be a protrusion 835 extending outward from and substantially perpendicular to a side face 810a-810d, and may include a slot 840. The lockable feature 830 may include a protrusion 845 directly extending from a side face 810a-810d, such that the protrusion 845 may be substantially parallel to and as an extension of the side face 810a-810d. The protrusion 845 may include tab 850, in which the tab 850 is insertable into the slot 840 of the locking feature 825. The tab 850 may be configured to be inserted in the slot 840 when the lid 805 is engaged with the container 805 (e.g., as shown by direction arrow "A"). The tab 850 may lock into the slot 840 in an interference fit, to maintain a closed configuration between the container 805 and the lid 805.

In embodiments, a liner 855, a first cover 860, and/or a second cover 865 may be removably attachable to or enclosable about a container 805 as described above with respect to FIGS. 6A-6D and FIG. 7 and as shown in FIGS. 8A-8C for illustrative purposes only.

Figure 9B:
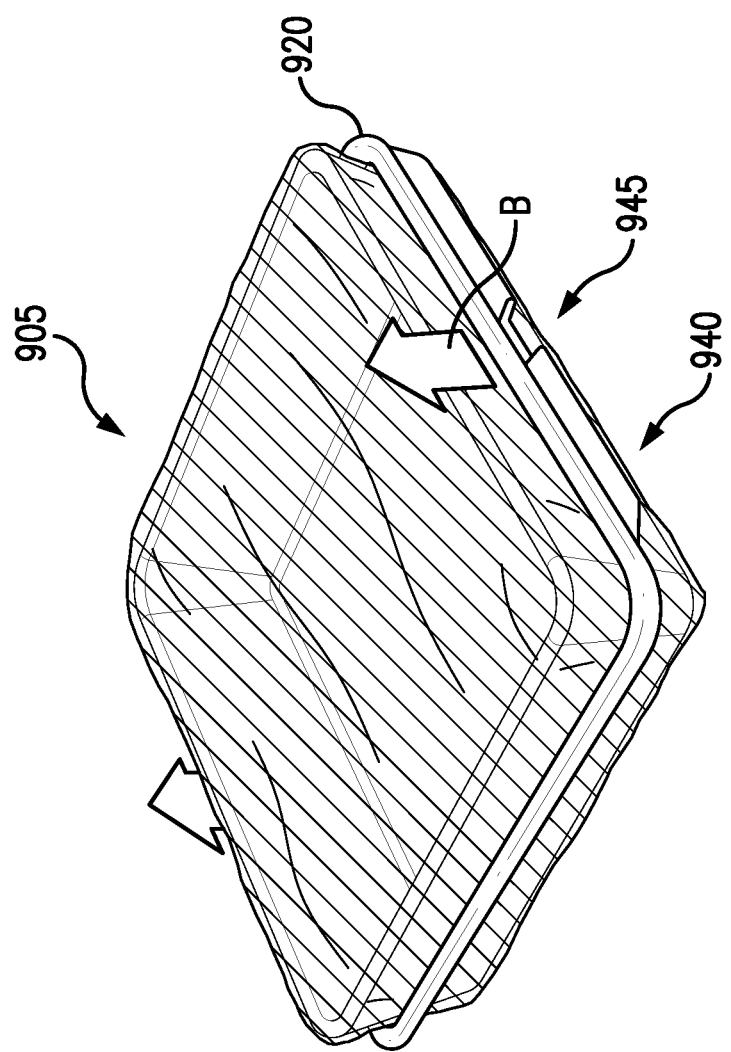

Referring now to FIGS. 9A-9B, another exemplary embodiment of a containment system 900 is shown. A container 905 may include side faces 910a-910d and bottom face 915 to form an inner portion 927. The side faces 910a-910d may be substantially straight, so a securement feature 920 may be engageable with the side faces 910a-

910d. In embodiments, the side faces 910a-910d may be angled outward from the bottom face 915, e.g., as a trapezoidal prism, so that a securement 920 may be engaged relative to the side faces 910a-910d. As the securement 920 slides upward from the bottom face 915 in direction of arrow "B", the angled side faces 910a-910d may engage with and lock against the securement 920 (see FIG. 9B).

The securement 920 may secure a liner 925, a first cover 930, and/or a second cover 935 around the container 905, and may be configured as a frame positionable around the container 905. In some embodiments, the liner 925 may be similar to the liner 600, and the first and/or second covers 930, 935 may be similar to the first and second covers 620, 635. For example, the liner 925, first cover 930, and/or second cover 935 may be extendable around the side faces 910a-910d in the direction of arrow "C". The liner 925, first cover 930 and/or second cover 935 may be formed as flat sheets, although in some embodiments, they may include closure features such as elastic, drawstring, or the like, as described above (see FIGS. 12A-12B).

The securement 920 may include one or more tabs 940. For example, tabs 940 may be disposed on opposing sides, so that in an attached configuration, the container 905 may be engage with rails of a transportation device, e.g., by the tabs 940. The tabs 940 may be protrusions extending outward in a substantially perpendicular direction, e.g., so that when engaged with rails of a transportation device, the container 905 may be held substantially parallel to the ground.

Figure 10B:
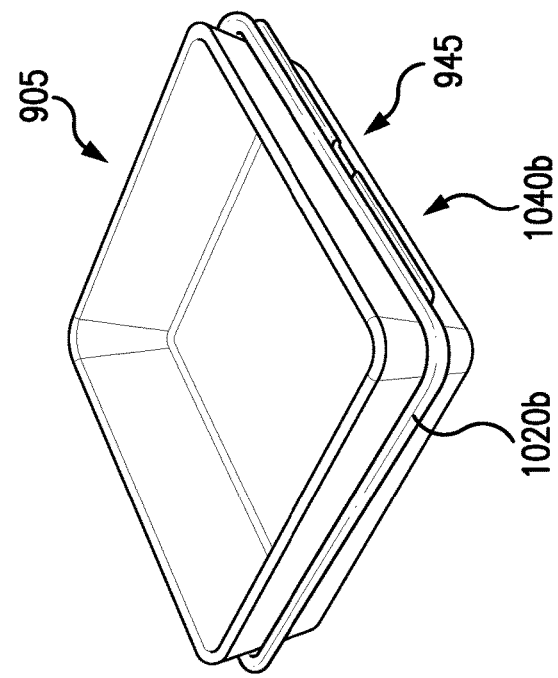
FIGS. 10A-10C illustrate exemplary embodiments of an adaptor for the containment system of FIGS. 9A-9B.
Figure 10A:
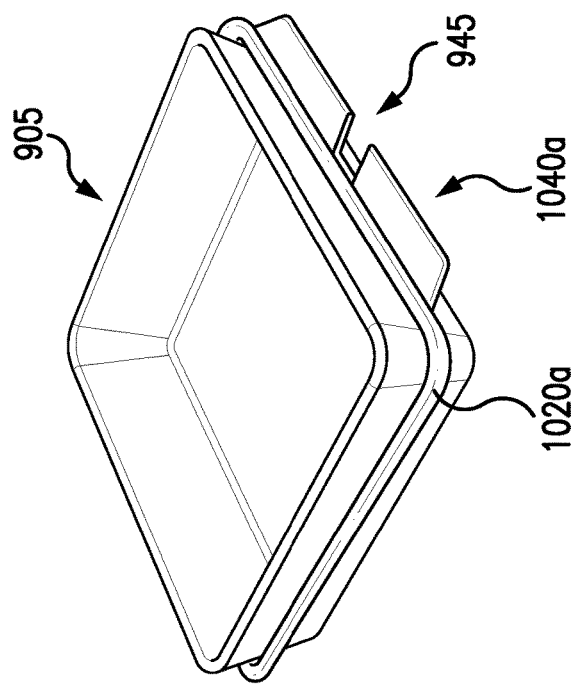
Figure 10C:
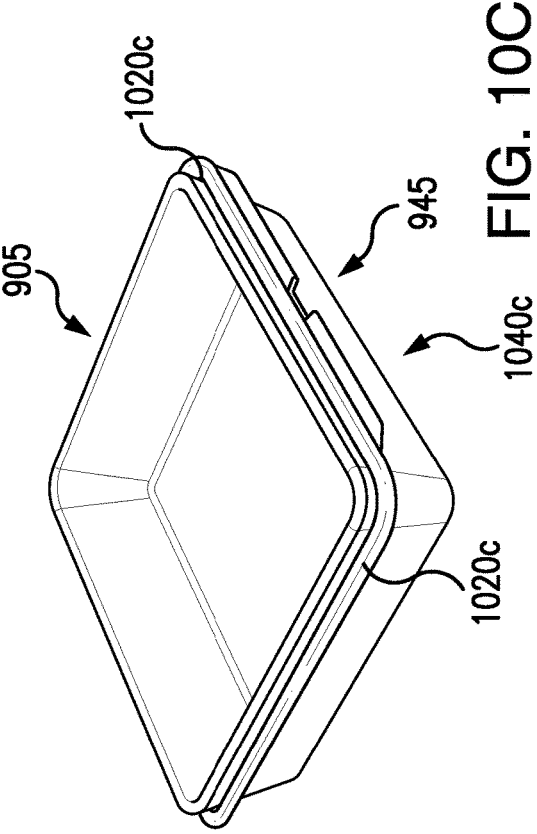

The securement 920 may allow for a container 905 to be adaptable to fit in a plurality of transportation devices. For example, a container may not be compatible with a selected transportation device, e.g., a transportation device already acquired by a medical facility. The securement 920 may be removably attachable to a container that may not otherwise engage with the selected transportation device, so that the tabs 940 may engage with the selected transportation device. As shown in FIGS. 10A-10C, respective tabs 1040a, 1040b, 1040c may be sized as desired so that the container 905 may be receivable in a plurality of transportation devices by using a selected securement 1020a, 1020b, 1020c. Additionally, since the securement 920, 1020a-1020c is removably attachable, the containers 905 may not be permanently altered, so that they may be otherwise compatible with other transportation devices without the securement 920, 1020a-1020c. In some embodiments, the securement 920, 1020a-1020c may include a cutout 945, which may act as a mating feature with a transportation device. For example, the cutout 945 may be mated with a corresponding protrusion on a transportation device, e.g., so that only the container 905 and securement 920, 1020a-1020c may be receivable into a selected transportation device.

Figure 12B:
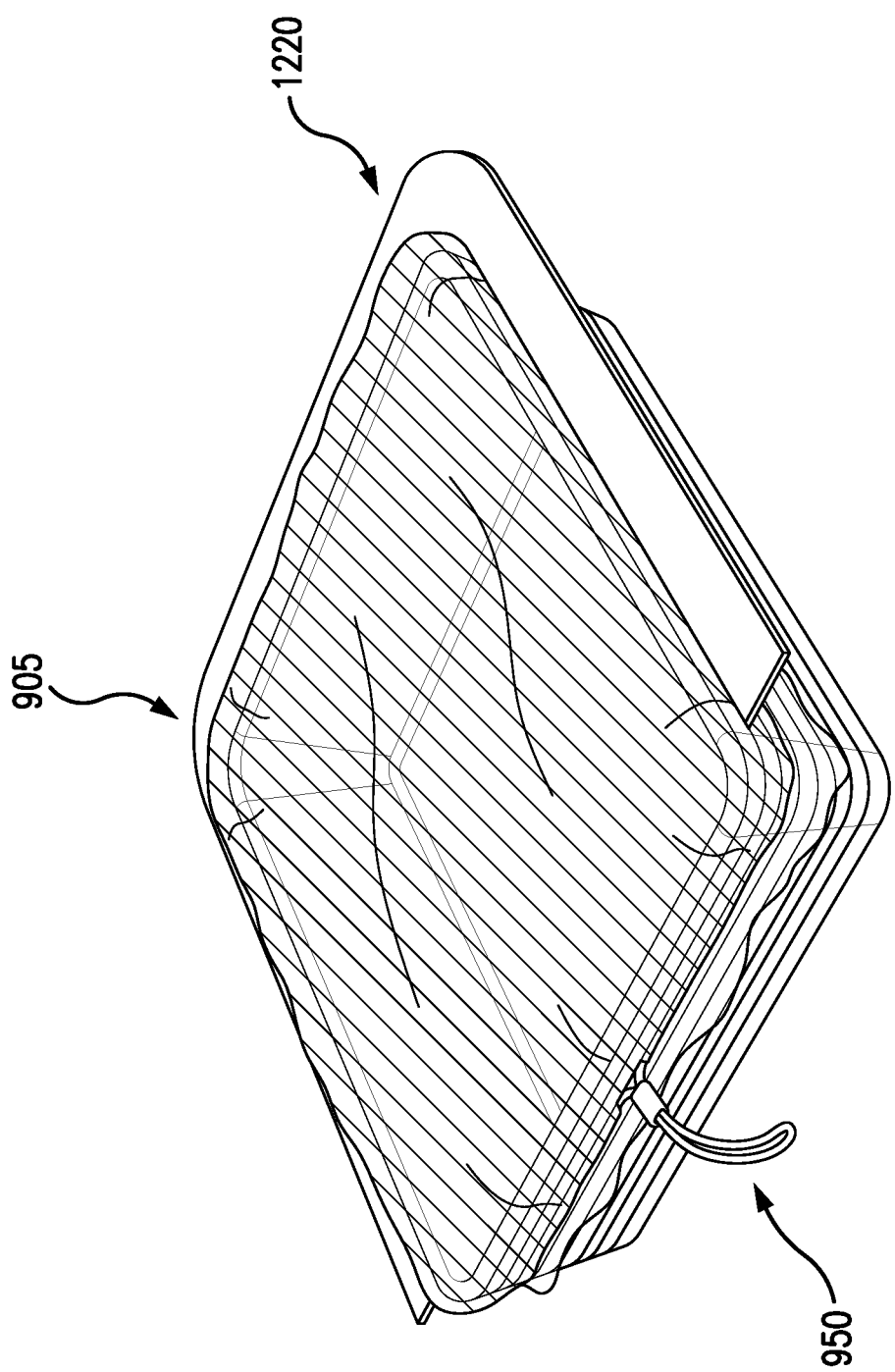
Figure 13A:
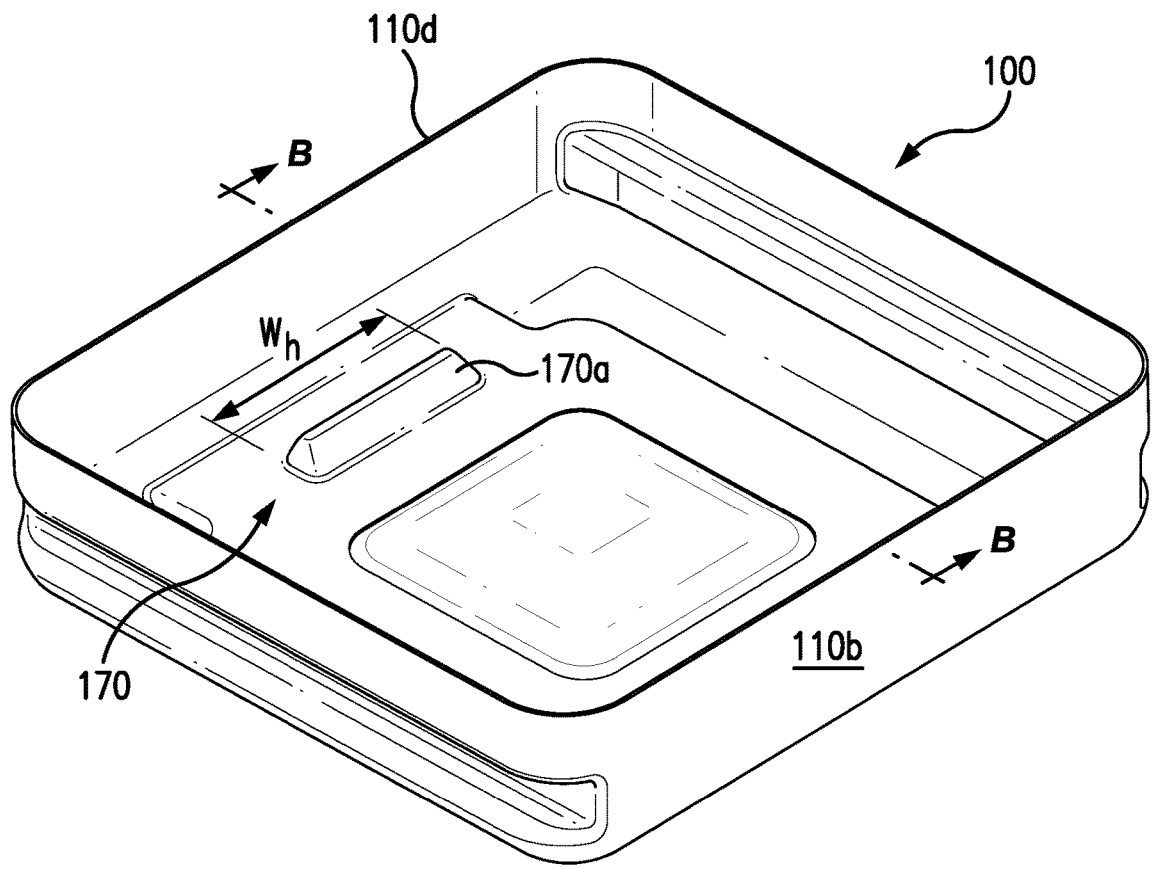
FIGS. 13A-13B illustrate an exemplary embodiment of a containment system with handle feature in accordance with the present disclosure
Figure 13B:
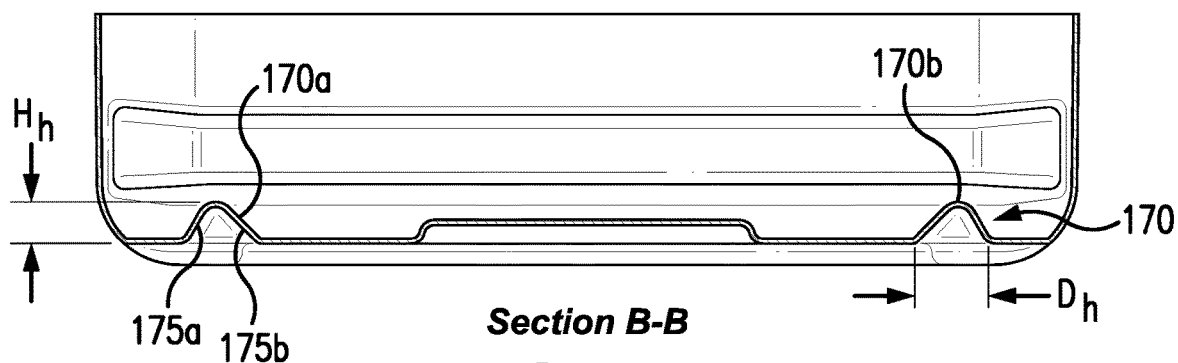

Although the securement 920, 1020a-1020c may be formed as a frame, e.g., having four sides to wholly surround the container 905, it is understood that a securement may be formed as a horseshoe, or U-shape. Referring now to FIGS. 12A-12B, securement 1220 may be removably attachable to a container 905. For example, the securement 1220 may engage with the container 905 by sliding the securement onto the container 905 in a direction indicated by arrow "D". Although one side face 910a-910d may be free of engagement with the securement 1220, the remaining three side faces 910a-910d may secure the liner 925, the first cover 930, and/or the second cover 935, and may engage with the transportation device as described above. As such, the liner 925, the first cover 930, and/or the second cover 935 may include a closure feature such as an elastic, drawstring, or the like, to otherwise engage with the side faces 910a-910d of the container 905.

Figure 11A:
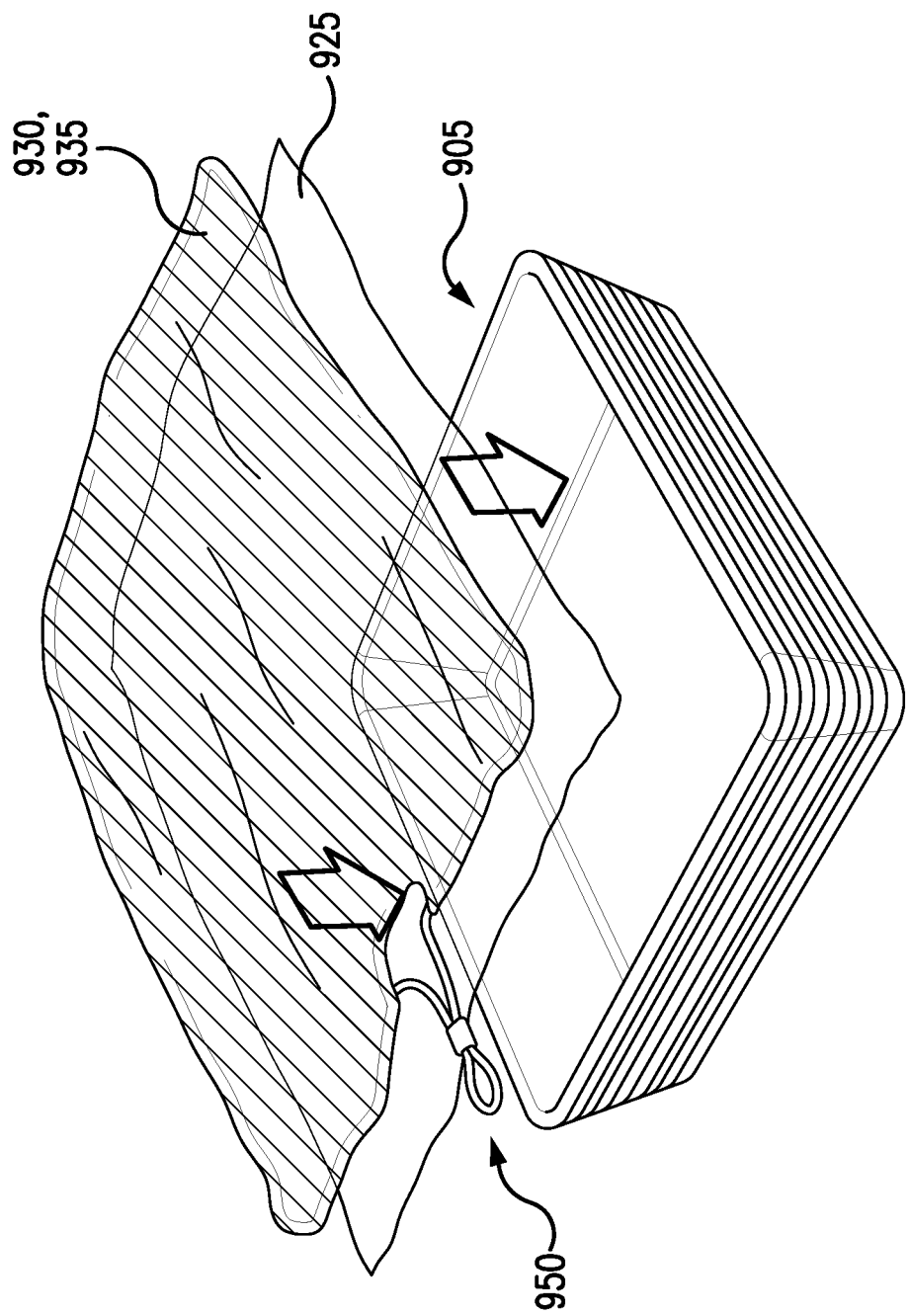
FIGS. 11A-11B illustrate an exemplary embodiment of a containment system in accordance with the present disclosure.
Figure 11B:
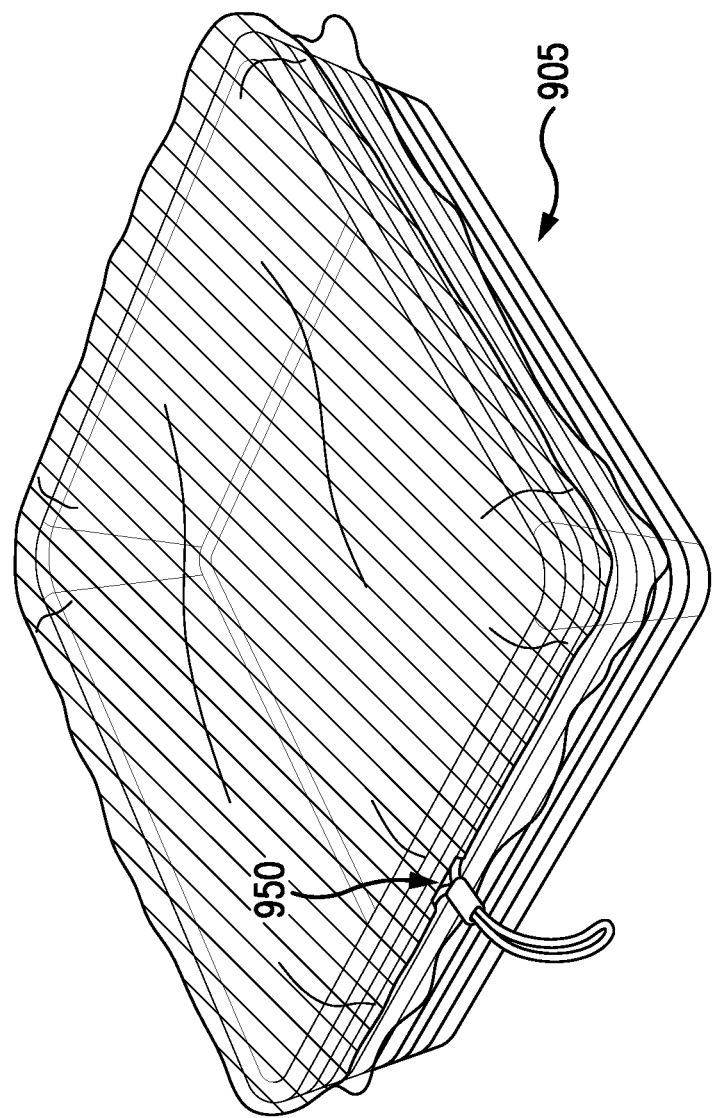

As shown in FIGS. 11A-11B, a liner 925, first cover 930, and/or second cover 935 may be removably attachable to or enclosable about the container 905 by a drawstring 950. For example, the liner 925, first cover 930, and/or second cover 935 may be formed as a sheet, having a drawstring 950 around a perimeter. To engage with the container 905, the drawstring 950 may be cinched around the side faces 910a-910d. The cinched drawstring 950 may maintain engagement with the container 905, e.g., before engagement of the securement 920, 1020a-1020c, 1220.

Referring to FIGS. 13A-13B, and FIGS. 14A-14B, alternative handle configurations are depicted for container 100. In some embodiments, e.g., FIG. 13A-13B, recessed portion 145 of bottom face 105 may incorporate bottom handle 170 to facilitate holding and movement of the container 100. Respective bottom handles 170a, 170b may be integrated into opposite sides of recessed portion 145 adjacent to side faces 110d, 110b. Handles 170a, 170b may be located in proximity to respective side faces 110d, 110b to allow for a user's fingertips to reach the handles. Each handle 170a, 170b may have a width $W_h$, height $H_h$ and depth $D_h$ dimension that is sized to accommodate the fingers of a user's hand grasping the container palm-side upward. For example, each handle 170a, 170b, may have a width $W_h$ that extends 3-7 in. (76.2-177.8 mm), a height $H_h$ that extends 0.5-2.0 in. (12.7-50.8 mm), and a depth $D_h$ that extends 0.5-2.0 in. (12.7-50.8 mm). Handles 170a, 170b, may extend inward from recessed portion 145 of bottom face 105 into the inner portion 125 of the container 100, and may include sloped faces 175a, 175b that meet at a point to form a triangle shape in cross-section and a wedge-shape along the width $W_h$ of the handles. Other shapes and dimensions for handles 170 may be possible, e.g., rectangular, depending on user requirements.

Figure 14A:
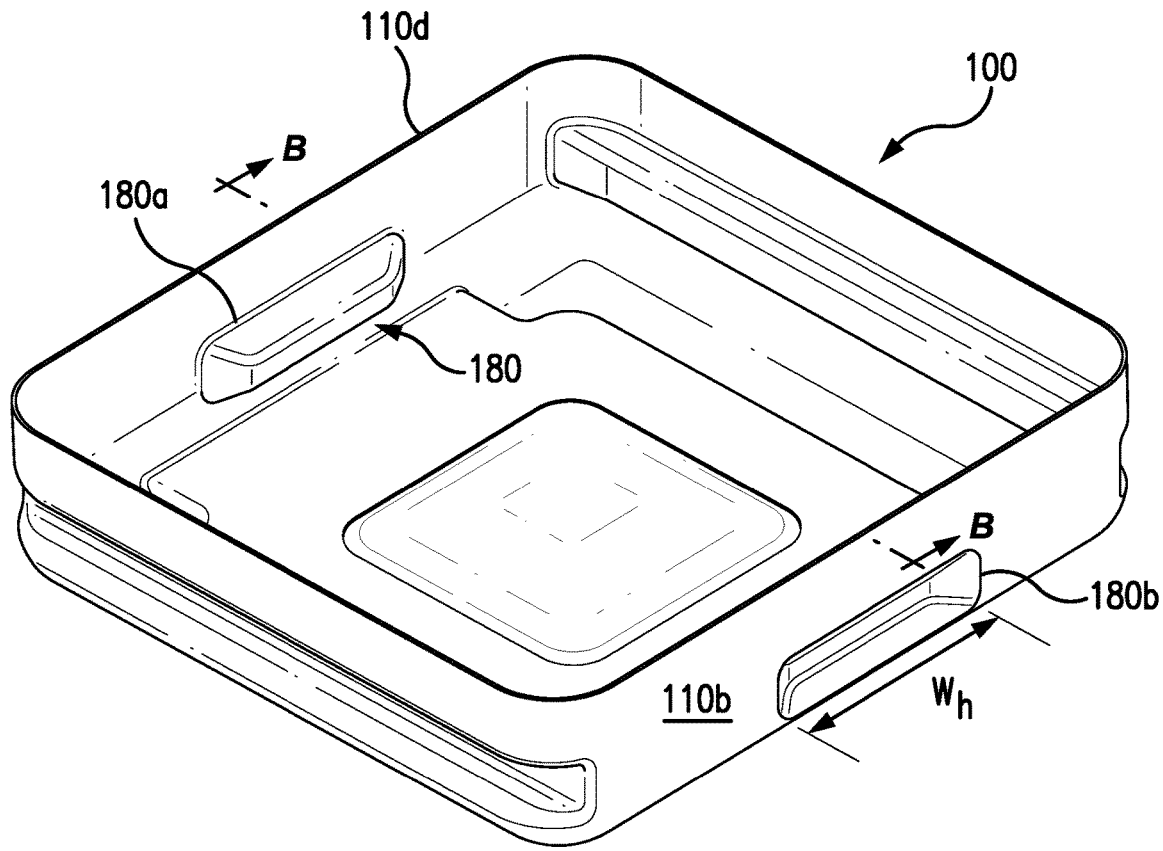
FIGS. 14A-14B illustrate an exemplary embodiment of a containment system with handle feature in accordance with the present disclosure.
Figure 14B:
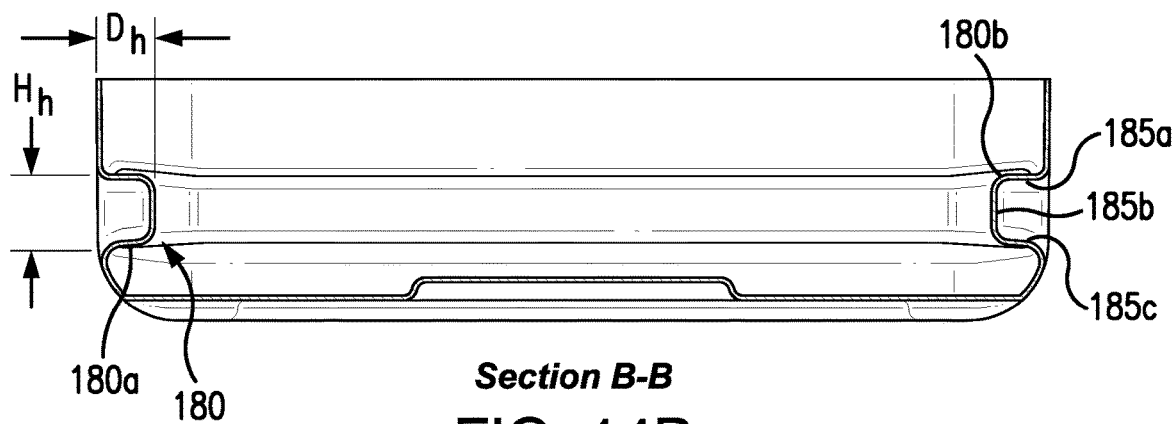

In some embodiments, e.g., FIGS. 14A-14B, side faces 110b, 110d may incorporate side handles 180 to facilitate holding and movement of the container 100. Respective side handles 180a, 180b may be integrated into opposite side faces 110d, 110b. Each side handle 180a, 180b may have a width $W_h$, height $H_h$ and depth $D_h$ dimension that is sized to accommodate the fingers of a user's hand grasping the container palm-side upward. For example, each handle 180a, 180b, may have a width $W_h$ that extends 3-7 in. (76.2-177.8 mm), a height fin that extends 1.0-2.0 in. (25.4-50.8 mm), and a depth $D_h$ that extends 0.5-2.0 in. (12.7-50.8 mm). Handles 180a, 180b, may extend inward from side faces 110d, 110b, respectively, into the inner portion 125 of the container 100. Handles 180a, 180b, similar to indentations 130, have surfaces 185a-185c formed substantially perpendicular to each other (90 degrees±10 degrees), although in some embodiments one or more of the surfaces may form an obtuse angle (≥90 degrees). Other shapes and dimensions for handles 180 may be possible depending on user requirements.

Bottom or side handles 170, 180, similar to corner handles 160, may provide a more secure grasping feature compared to holding a container from the bottom face 105 and/or side faces 110a-110d, particularly if the container is encased in a liner 600.

Figure 15:
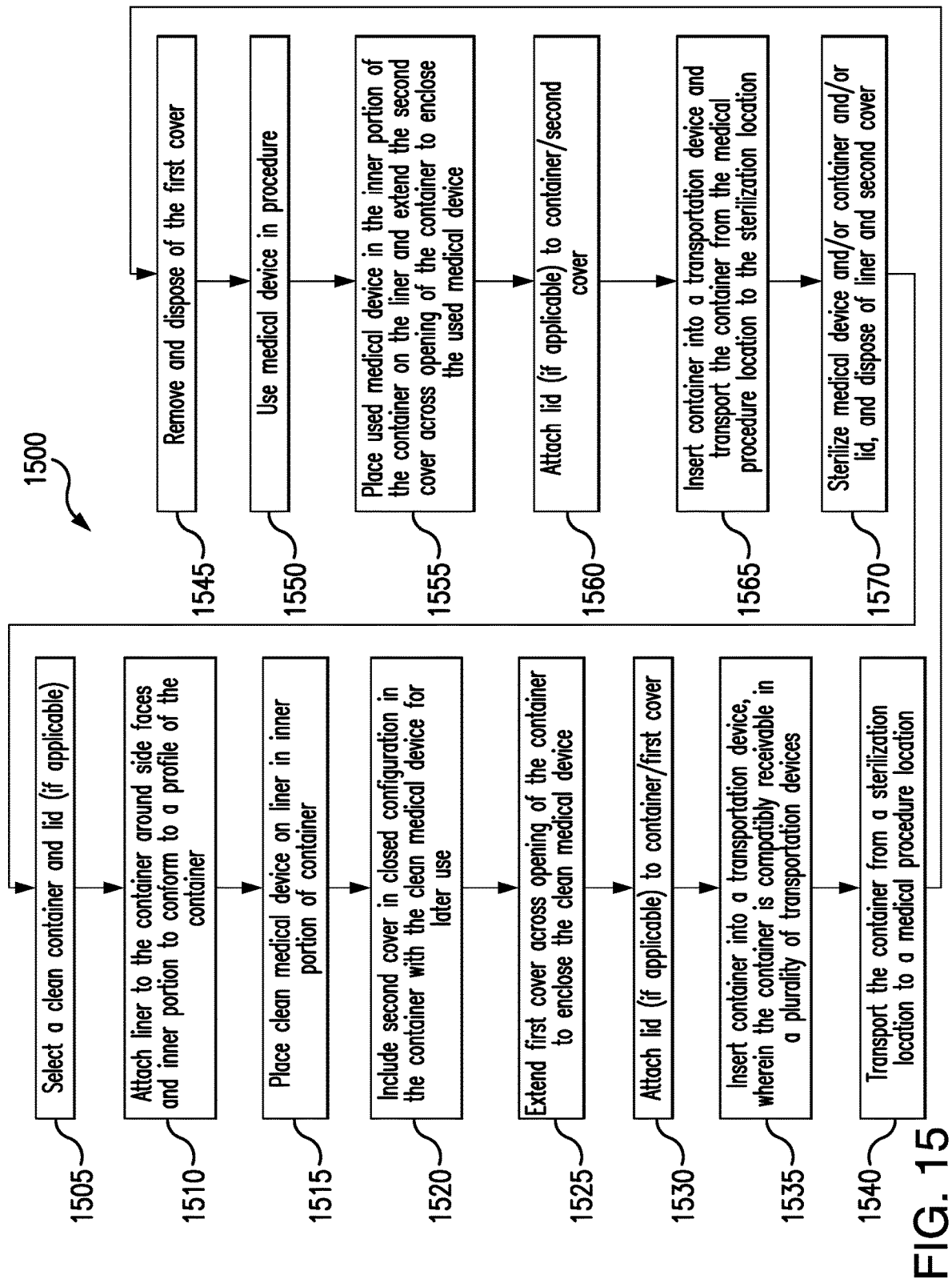
FIG. 15 illustrates a flow chart of an exemplary embodiment of a method for containing and transporting a medical device in accordance with the present disclosure.

Referring now to FIG. 15, a flow chart 1500 of an exemplary method of containing and transporting a medical device is illustrated. At step 1505, a medical professional may select a clean container and lid (if applicable), for containing and transporting a clean medical device. The medical professional may be in a reprocessing location at a medical facility, where containers and medical devices are processed and cleaned between patient procedures. A clean liner may be attached to the clean container, extending at least partially around the side faces and the inner portion of the container, to conform to a profile of the container at step 1510. A clean medical device may be placed on the liner in the inner portion of the container at step 1515, and a second cover may be included in the inner portion of the container in a closed configuration (e.g., folded) for later use at step 1520. In some embodiments, the second cover may not be included in the container, but may be separately available at the medical procedure location. A first cover may be tautly extended across the opening of the container to enclose the medical device between the liner and the cover in the container at step 1525. As described above, the first cover may be green, or other pattern, to visually indicate a clean medical device is enclosed in the container. At step 1530, a lid may be optionally attached to the container and/or first cover.

The container may be inserted into a transportation device, e.g., by indentations and/or protrusions to engage with corresponding rails, at step 1535. The container may be compatibly receivable into a plurality of transportation devices by the indentations, protrusions, and/or other securement features on the container. At step 1540, one or more containers may be transported from the reprocessing location to a medical procedure location in the medical facility by the transportation device.

When the container is delivered to the medical procedure location, a medical professional may remove the lid (if attached), and the first cover may be removed and disposed of at step 1545, in anticipation of use of the medical device. The second cover may be placed aside for after the procedure, and/or a second cover may be obtained for later use. The medical professional may then use the medical device in a procedure on a patient at step 1550. For example, when the medical device is a reusable endoscope, the endoscope may be inserted into the patient for performing the procedure as desired.

Upon completion of the procedure, the used medical device may be placed on the liner in the inner portion of the container at step 1555. The second cover may then be extended across the opening of the container to enclose the used medical device between the liner and the second cover. In embodiments, the second cover may be colored red, or patterned, as a visual indication that the medical device is used. At step 1560, the lid may optionally be attached to the container and the second cover.

The container may be inserted into the transportation device at step 1565 in the same manner as in step 1535. The transportation device may transport the container from the medical procedure location back to the reprocessing location in the medical facility for cleaning. At step 1570, the used medical device may be removed from the container and cleaned for reuse. The second cover and the liner may be disposed of, and the container and lid (if applicable) may also be cleaned. The method may return to step 1505 for further selection of a clean medical device and container for use.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for containing and transporting a medical device, the system comprising:
    a container including a bottom face and surrounding side faces as a closed first end and an open second end to form an inner portion for receiving and retaining the medical device, at least a portion of one or more of the side faces having an indentation extending along a length of the respective side face; and
    a liner removably enclosable about the container, the liner being extendable over the side faces to line the inner portion of the container and extending fully over the side faces to an outer surface of the bottom face of the container, such that the liner is conformable to a profile of the container;
    wherein the indentation on at least a portion of the one or more side faces is formed into the inner portion of the container such that the container is compatibly receivable in a first transportation device in a first orientation, the indentation having a flared end opening.

2. The system according to claim 1, wherein the bottom face of the container includes a contour, such that the container is compatibly receivable in the first transportation device in a second orientation different from the first orientation.

3. The system according to claim 1, further comprising a lid removably attachable to the open second end of the container, the lid being extendable over the side faces to enclose the inner portion of the container.

4. The system of claim 1, further comprising:
a lid removably attachable to the open second end of the container, the lid being at least partially insertable in the inner portion of the container, such that an overhang of the lid contacts with an upper edge of the side faces of the container.

5. The system according to claim 3, wherein a contour of the lid is formed to mate with a bottom face contour of the container, such that a plurality of containers and lids are stackable in alignment with each other.

6. The system according to claim 3, wherein the lid includes one or more handles.

7. The system according to claim 1, further comprising:
a first cover removably enclosable about the container and extendable over at least a portion of the side faces and across the open second end of the container to enclose the inner portion; and
a second cover removably enclosable about the container and extendable over at least a portion of the side faces and across the open second end of the container to enclose the inner portion;
wherein the first cover is exchangeable with the second cover; and
wherein the first cover is visually different from the second cover, thereby allowing for visual verification of a condition of the medical device.

8. The system according to claim 1, wherein the container is compatibly receivable in a second transportation device, the second transportation device different from the first transportation device, such that the container is exchangeable between the first transportation device and the second transportation device.

9. The system according to claim 1, wherein the liner is removably enclosable about the container by an elastic opening or drawstring.

10. A method for containing and transporting a medical device using the system of claim 1, comprising:
enclosing the liner about the container;
receiving the medical device in the inner portion of the container; and
enclosing a first cover about the container, extending over at least a portion of the side faces and across the open second end of the container to enclose the inner portion, wherein the first cover is exchangeable with a second cover for visual verification of a condition of the medical device.

11. The method according to claim 10, wherein the bottom face of the container includes a contour, such that the container is compatibly receivable in the first transportation device in a second orientation different from the first orientation.

12. The method according to claim 10, further comprising attaching a lid to the open second end of the container to enclose the inner portion of the container.

13. The method according to claim 10, wherein the container is compatibly receivable in a second transportation device, the second transportation device different from the first transportation device, such that the container is exchangeable between the first transportation device and the second transportation device.

14. The method according to claim 10, further comprising exchanging the first cover and the second cover in response to a change in the condition of the medical device.

* * * * *